United States Patent
Pettis et al.

(10) Patent No.: US 9,242,052 B2
(45) Date of Patent: *Jan. 26, 2016

(54) METHOD FOR ALTERING DRUG PHARMACOKINETICS BASED ON MEDICAL DELIVERY PLATFORM

(71) Applicant: Becton Dickinson and Company, Franklin Lakes, NJ (US)

(72) Inventors: Ronald J Pettis, Cary, NC (US); Noel G Harvey, Efland, NC (US); James A Down, Randolph, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/215,271

(22) Filed: Mar. 17, 2014

(65) Prior Publication Data

US 2014/0200547 A1 Jul. 17, 2014

Related U.S. Application Data

(60) Continuation of application No. 13/072,824, filed on Mar. 28, 2011, now Pat. No. 8,708,994, which is a continuation of application No. 12/100,259, filed on Apr. 9, 2008, now abandoned, which is a division of (Continued)

(51) Int. Cl.
*A61M 5/158* (2006.01)
*A61M 5/46* (2006.01)
(Continued)

(52) U.S. Cl.
CPC .............. *A61M 5/46* (2013.01); *A61K 38/28* (2013.01); *A61K 38/29* (2013.01); *A61M 5/158* (2013.01); *A61M 5/32* (2013.01); *A61M 5/3286* (2013.01); *A61M 5/3291* (2013.01); *A61M 5/3295* (2013.01); *A61M 37/0015* (2013.01);
(Continued)

(58) Field of Classification Search
CPC ...... A61M 5/158; A61M 5/32; A61M 5/3286; A61M 5/46; A61M 37/0015; A61M 2037/0061
See application file for complete search history.

(56) References Cited

U.S. PATENT DOCUMENTS 2,619,962 A 12/1952 Rosenthal
3,814,097 A 6/1974 Ganderton et al.
(Continued)

FOREIGN PATENT DOCUMENTS

CA 2349431 5/2000
EP 0692270 1/1996
(Continued)

OTHER PUBLICATIONS

Agrawal et al., 1991, "Pharmacokinetics, Biodistribution, and Stability of Oligodeoxynucleotide Phosphorothioates in Mice," Proc. Natl. Acad. Sci. USA 88:7595-7599.
(Continued)

*Primary Examiner* — Laura Bouchelle
(74) *Attorney, Agent, or Firm* — The Webb Law Firm

(57) ABSTRACT

A method for directly delivering whereby a substance is introduced into an intradermal space within mammalian skin which involves administering the substance through at least one small gauge hollow needle having an outlet with an exposed height between 0 and 1 mm. The outlet is inserted into the skin to a depth of between 0.3 mm and 2 mm such that the delivery of the substance occurs at a depth between 0.3 mm and 2 mm.

20 Claims, 10 Drawing Sheets

Related U.S. Application Data application No. 09/893,746, filed on Jun. 29, 2001, now abandoned, which is a continuation-in-part of application No. 09/606,909, filed on Jun. 29, 2000, now Pat. No. 8,465,468.

(51) Int. Cl.
| | | |
|---|---|---|
| *A61M 5/32* | (2006.01) | |
| *A61M 37/00* | (2006.01) | |
| *A61K 38/28* | (2006.01) | |
| *A61K 38/29* | (2006.01) | |

(52) U.S. Cl.
CPC .............. *A61M2037/0038* (2013.01); *A61M 2037/0061* (2013.01)

(56) References Cited

U.S. PATENT DOCUMENTS

| | | | |
|---|---|---|---|
| 3,964,482 A | 6/1976 | Gerstel et al. | |
| 4,270,537 A | 6/1981 | Romaine | |
| 4,440,207 A | 4/1984 | Genatempo et al. | |
| 4,512,767 A | 4/1985 | Denance | |
| 4,592,753 A | 6/1986 | Panoz | |
| 4,655,762 A | 4/1987 | Rogers | |
| 4,886,499 A | 12/1989 | Cirelli et al. | |
| 5,003,987 A | 4/1991 | Grinwald | |
| 5,098,389 A | 3/1992 | Cappucci | |
| 5,156,591 A | 10/1992 | Gross et al. | |
| 5,242,425 A | 9/1993 | White et al. | |
| 5,250,023 A | 10/1993 | Lee et al. | |
| 5,279,544 A | 1/1994 | Gross et al. | |
| 5,279,552 A | 1/1994 | Magnet | |
| 5,340,359 A | 8/1994 | Segura Badia | |
| 5,417,662 A | 5/1995 | Hjertman et al. | |
| 5,484,417 A | 1/1996 | Waitz et al. | |
| 5,505,694 A | 4/1996 | Hubbard et al. | |
| 5,527,288 A | 6/1996 | Gross et al. | |
| 5,536,258 A | 7/1996 | Folden | |
| 5,567,495 A | 10/1996 | Modak et al. | |
| 5,582,591 A | 12/1996 | Cheikh | |
| 5,591,139 A | 1/1997 | Lin et al. | |
| 5,741,224 A | 4/1998 | Milder et al. | |
| 5,792,120 A | 8/1998 | Menyhay | |
| 5,800,420 A | 9/1998 | Gross et al. | |
| 5,801,057 A | 9/1998 | Smart et al. | |
| 5,807,375 A | 9/1998 | Gross et al. | |
| 5,820,622 A | 10/1998 | Gross et al. | |
| 5,848,990 A | 12/1998 | Cirelli et al. | |
| 5,848,991 A | 12/1998 | Gross et al. | |
| 5,876,582 A | 3/1999 | Frazier | |
| 5,879,326 A | 3/1999 | Godshall et al. | |
| 5,925,739 A | 7/1999 | Spira et al. | |
| 5,928,207 A | 7/1999 | Pisano et al. | |
| 5,957,895 A | 9/1999 | Sage et al. | |
| 5,997,501 A | 12/1999 | Gross et al. | |
| 6,007,821 A | 12/1999 | Srivastava et al. | |
| 6,056,176 A | 5/2000 | Aftanas et al. | |
| 6,056,716 A | 5/2000 | D'Antonio et al. | |
| 6,099,504 A | 8/2000 | Gross et al. | |
| 6,200,291 B1 | 3/2001 | Di Pietro | |
| 6,256,533 B1 | 7/2001 | Yuzhakov et al. | |
| 6,319,224 B1 | 11/2001 | Stout et al. | |
| 6,334,856 B1 | 1/2002 | Allen et al. | |
| 6,346,095 B1 | 2/2002 | Gross et al. | |
| 6,482,176 B1 | 11/2002 | Wich | |
| 6,494,865 B1 | 12/2002 | Alchas | |
| 6,537,242 B1 | 3/2003 | Palmer | |
| 6,569,143 B2 | 5/2003 | Alchas et al. | |
| 6,591,133 B1 | 7/2003 | Joshi | |
| 6,607,513 B1 | 8/2003 | Down et al. | |
| 6,611,707 B1 | 8/2003 | Prausnitz et al. | |
| 6,623,457 B1 | 9/2003 | Rosenberg | |
| 6,679,870 B1 | 1/2004 | Finch et al. | |
| 6,743,211 B1 | 6/2004 | Prausnitz et al. | |
| 6,808,506 B2 | 10/2004 | Lastovich et al. | |
| 7,722,595 B2 | 5/2010 | Pettis et al. | |
| 8,465,468 B1 * | 6/2013 | Pettis et al. | 604/506 |
| 8,708,994 B2 * | 4/2014 | Pettis et al. | 604/506 |
| 2001/0056263 A1 | 12/2001 | Alchas et al. | |
| 2002/0038111 A1 | 3/2002 | Alchas et al. | |
| 2002/0095134 A1 | 7/2002 | Pettis et al. | |
| 2002/0156453 A1 | 10/2002 | Pettis et al. | |
| 2003/0073609 A1 | 4/2003 | Pinkerton | |
| 2003/0093032 A1 | 5/2003 | Py et al. | |
| 2003/0100885 A1 | 5/2003 | Pettis et al. | |
| 2004/0028707 A1 | 2/2004 | Pinkerton | |
| 2004/0073160 A1 | 4/2004 | Pinkerton | |
| 2004/0082934 A1 | 4/2004 | Pettis et al. | |
| 2004/0170654 A1 | 9/2004 | Pinkerton | |
| 2004/0175360 A1 | 9/2004 | Pettis et al. | |
| 2004/0175401 A1 | 9/2004 | Pinkerton | |
| 2005/0008683 A1 | 1/2005 | Mikszta et al. | |
| 2005/0010193 A1 | 1/2005 | Laurent et al. | |
| 2005/0096330 A1 | 5/2005 | Boettcher et al. | |
| 2005/0096331 A1 | 5/2005 | Das et al. | |
| 2005/0096332 A1 | 5/2005 | Jung et al. | |
| 2005/0096630 A1 | 5/2005 | Pettis et al. | |
| 2005/0096631 A1 | 5/2005 | Pettis et al. | |
| 2005/0096632 A1 | 5/2005 | Pettis et al. | |
| 2005/0124967 A1 | 6/2005 | Kaestner et al. | |
| 2005/0147525 A1 | 7/2005 | Bousquet | |
| 2005/0181033 A1 | 8/2005 | Dekker, III et al. | |
| 2005/0196380 A1 | 9/2005 | Mikszta et al. | |
| 2005/0245594 A1 | 11/2005 | Sutter et al. | |
| 2005/0256182 A1 | 11/2005 | Sutter et al. | |
| 2005/0256499 A1 | 11/2005 | Pettis et al. | |
| 2008/0118465 A1 | 5/2008 | Pettis et al. | |
| 2008/0118507 A1 | 5/2008 | Pettis et al. | |
| 2008/0119392 A1 | 5/2008 | Pettis et al. | |
| 2008/0138286 A1 | 6/2008 | Pettis et al. | |
| 2008/0140050 A1 | 6/2008 | Pettis et al. | |
| 2008/0147042 A1 | 6/2008 | Pettis et al. | |
| 2008/0234656 A1 | 9/2008 | Pettis et al. | |
| 2009/0124997 A1 | 5/2009 | Pettis et al. | |
| 2011/0190725 A1 | 8/2011 | Pettis et al. | |
| 2013/0237960 A1 | 9/2013 | Pettis et al. | |
| 2013/0237961 A1 | 9/2013 | Pettis et al. | |
| 2013/0245601 A1 | 9/2013 | Pettis et al. | |

FOREIGN PATENT DOCUMENTS

| | | |
|---|---|---|
| EP | 0429842 B1 | 8/1996 |
| EP | 1086718 A1 | 3/2001 |
| EP | 1086719 A1 | 3/2001 |
| EP | 1088642 A1 | 4/2001 |
| EP | 1092444 A1 | 4/2001 |
| EP | 1246668 B1 | 10/2002 |
| EP | 1296740 B1 | 11/2007 |
| JP | A 113862 | 3/1999 |
| WO | WO 94/23777 A1 | 10/1984 |
| WO | WO 87/00441 A1 | 1/1987 |
| WO | WO 93/17754 A1 | 9/1993 |
| WO | WO 96/17648 A1 | 6/1996 |
| WO | WO 96/37155 A1 | 11/1996 |
| WO | WO 96/37256 A1 | 11/1996 |
| WO | WO 97/21457 A1 | 6/1997 |
| WO | WO 99/43350 A1 | 9/1999 |
| WO | WO 99/64580 A1 | 12/1999 |
| WO | WO 00/09186 A2 | 2/2000 |
| WO | WO 00/16833 A1 | 3/2000 |
| WO | WO 00/67647 A1 | 11/2000 |
| WO | WO 00/74763 A2 | 12/2000 |
| WO | WO 01/39772 A1 | 6/2001 |
| WO | WO 02/02178 A1 | 1/2002 |
| WO | WO 02/02179 A1 | 1/2002 |
| WO | WO 02/11669 A2 | 2/2002 |
| WO | WO 02/083231 A1 | 10/2002 |
| WO | WO 02/083232 A1 | 10/2002 |
| WO | WO 03/002175 A2 | 1/2003 |
| WO | WO 03/015787 A1 | 2/2003 |
| WO | WO 03/057143 A2 | 7/2003 |
| WO | WO 2004/098676 A2 | 11/2004 |

(56) References Cited

FOREIGN PATENT DOCUMENTS

| WO | WO 2004/101023 A2 | 11/2004 |
|---|---|---|
| WO | WO 2005/086773 A2 | 9/2005 |
| WO | WO 2005/115360 A2 | 12/2005 |

OTHER PUBLICATIONS

Anon, 2004, "Flu vaccine: skin injection method effective in younger people," American Health Line: Research Notes (Nov. 4, 2004).
Autret et al., 1989, "Comparison of Pharmacokinetics and tolerance of Calcitonine administered by Intradermal or Subcutaneous Route," Fundamental Clinical Pharmacology 3(2):170-171.
Autret et al., 1991, "Comparaison des concentrations plasmatiques et de la tolerance d'une dose unique de calcitonine humaine administree par voie intradermique et sous-cutanee," Therapie 46:5-8 (with English Translation).
Ba Wu et al., 1989, "Pharmacokinetics of Methoxyflurane after its Intra-Dermal Inection as Lecithin-Coated Microdroplets," Journal of Controlled Release 9:1-12.
Bader, 1980, "Influenza vaccine experience in Seattle," Am. J. Public Health 70(5):545.
Belshe et al., 2004, "Serum antibody responses after intradermal vaccination against influenza," New England Journal of Medicine 351(22):2286-2294.
Benoni et al., 1984, "Distribution of Ceftazidime in Ascitic Fluid", Antimicrobial Agents and Chemotherapy 25(6):760-763.
Bickers et al., editors, 1984, "Clinical Pharmacology of Skin Disease", Churchill Livingstone, Inc.:57-90.
Bocci et al., 1986, "The Lymphatic Route. IV. Pharmacokinetics of Human Recombinant Interferon a2 and Natural Interferon β Administered Intradermally in Rabbits", International Journal of Phamaceutics 32:103-110.
Branswell, 2004, "Vaccine stretching may be an option for future shortages, pandemics: studies," Canadian Press News Wire (Nov. 3, 2004).
Bresolle et al., 1993, "A Weibull Distribution Model for Intradermal Administration of Ceftazidime", Journal of Pharmaceutical Sciences 82(11):1175-1178.
Bronaugh et al., 1982, "Methods for in Vitro Percutaneous Absorption Studies. II. Animal Models for Human Skin," Toxicol. and Applied Pharmacol. 62(3):481-488.
Brooks et al., 1977, "Intradermal administration of bivalent and monovalent influenza vaccines," Ann. Allergy 39(2):110-112.
Brown et al., 1977, "The immunizing effect of influenza A/New Jersey/76 (Hsw1N1) virus vaccine administered intradermally and intramuscularly to adults," J. Infect. Dis. 136 Suppl:S466-71.
Burkoth et al., 1999, "Transdermal and Transmucosal Powered Drug Delivery," Critical Review in Therapeutic Drug Carrier Systems 16(4):331-384.
Callen, 1981, "Intralesional Corticosteriods", Journal of the American Academy of Dermatology, University of Louisville School of Medicine, 149-151.
Communication of a Notice of Opposition to EP 1296740 (Aug. 14, 2008) and Opposition Brief in its entirety.
Communication of a Notice of Opposition to EP 1296740 (Jul. 18, 2008) and Opposition Brief in its entirety.
Corbo et al., 1989, "Transdermal Controlled Delivery of Propranolol from a Multilaminate Adhesive Device," Pharm. Res. 6(9):753-758.
Cossum et al., 1993, "Disposition of the C-Labeled Phosphorothioate Oligonucleotide ISIS 2105 after Intravenous Administration to Rats", The Journal of Pharmacology and Experimental Therapeutics 267(3):1181-1190.
Cossum et al., 1994, "Pharmacokinetics of C-Labeled Phosphorothioate Olignucleotide, ISIS 2105 after Administration to Rats", The Journal of Pharmacology and Experimental Therapeutics, 269(1):89-94.
Crooke et al., 1994, "A Pharmacokinetic Evaluation of C-Labeled Afovirsen Sodium in Patients with Genital Warts", Clinical Pharmacology & Therapeutics 56(6):641-646.
Crowe, 1965, "Experimental comparison of intradermal and subcutaneous vaccination with influenza vaccine," Am. J. Med. Technol. 31(6):387-396.
Decision of Opposition Division Revoking EP 1296742 (Mar. 27, 2008).
Erstad et. al., 1993, "Influence of Injection Site and Route on Medication Absorption," Hospital Pharmacy 28(9), 853-854, 872-873.
Firooz et al., 1995, "Benefits and Risks of Intralesional Corticosteroid Injection in the Treatment of Dermatological Diseases", Clinical and Experimental Dermatology 20(5):363-370.
First Page of Lantus draft Product Insert submitted to the FDA (Apr. 2000).
Fjerstad, 2004, "U. Minnesota professor uses alternative flu vaccine technique," FSView & Florida Flambeau via U-Wire (Nov. 15, 2004).
Foy et al., 1970, "Efficacy of intradermally administered A2 Hong Kong vaccine," JAMA 213(1):130.
Glenn et al., 1999, "Advances in vaccine delivery: transcutaneous immunisation," Exp. Opin. Invest. Drugs 8(6):797-805.
Goodarzi et al., 1992, "Organ Distribution and Stability of Phosphorothioted Oligodeoxyribonucleotides in Mice," Biopharmaceutics & Drug Disposition 13(3):221-227.
Gramzinski et al., 1998, "Immune response to a hepatitis B DNA vaccine in Aotus monkeys: a comparison of vaccine formulation, route, and method of administration," Mol. Med. 4(2):109-118.
Halperin et al., 1979, "A comparison of the intradermal and subcutaneous routes of influenza vaccination with A/New Jersey/76 (swine flu) and A/Victoria/75: report of a study and review of the literature," Am. J. Public Health. 69(12):1247-1250.
Haynes et al., 1985, "Ultra-long-duration Local Anesthesia Produced by Injection of Lecithin-coated Methoxyflurane Microdroplets", Anestheiology 63(5):490-499.
Henry et al., 1998, "Microfabricated Microneedles: A Novel Approach to Transdermal Drug Delivery", Journal of Pharmaceutical Sciences 87(8):922-925.
Herbert et al., 1979, "Comparison of responses to influenza A/New Jersey/76-A/Victoria/75 virus vaccine administered intradermally or subcutaneously to adults with chronic respiratory disease," J. Infect. Dis. 140(2):234-238.
International Search Report mailed Apr. 21, 2006 from the International Searching Authority for PCT/US2004/014469, filed May 6, 2004.
International Search Report mailed Dec. 11, 2001 from the International Searching Authority for PCT/US2001/020763, filed Jun. 29, 2001.
International Search Report mailed Dec. 11, 2001 from the International Searching Authority for PCT/US2001/020782, filed Jun. 29, 2001.
International Search Report mailed Dec. 14, 2006 from the International Searching Authority for PCT/US2004/014033, filed May 6, 2004.
International Search Report mailed Dec. 6, 2006 from the International Searching Authority for PCT/US2005/07412, filed Mar. 8, 2005.
International Search Report mailed Oct. 6, 2003 from the International Searching Authority for PCT/US2002/040841, filed Dec. 23, 2002.
International Search Report mailed Sep. 18, 2006 from the International Searching Authority for PCT/US2005/016424, filed May 11, 2005.
International Search Report mailed Sep. 2, 2002 from the International Searching Authority for PCT/US2001/50436, filed Dec. 28, 2001.
International Search Report mailed Sep. 3, 2002 from the International Searching Authority for PCT/US2001/50440, filed Dec. 28, 2001.
International Standard ISO 9626, Stainless steel needle tubing for the manufacture of medical devices, p. 2 (Table 2—Dimensions of Tubing) of ISO 9626, 1st Edition, Sep. 1, 1991, Amendment 1, Jun. 1, 2001.
Jakobson et al., 1977, "Variations in the Blood Concentration of 1,1,2-Trichloroethane by Percutaneous Absorption and Other Routes of Administrtion in the Guinea Pig", Acta Pharmacologica et Toxicologica 41(5):497-506.

(56) References Cited

OTHER PUBLICATIONS

Jarratt et al., 1974, "The Effects of Intradermal Steriods on the Pituitary-Adrenal Axis and the Skin", Journal of Investigative Dermatology 62(4):463-466.
Kaushik et al., 1999, "Transdermal Protein Delivery Using Microfabricated Microneedles", 1 page.
Kenny et al., 2004, "Dose sparing with intradermal injection of influenza vaccine," New England Journal of Medicine 351(22):2295-2301.
Kirkpatrick et al., 1987, "Local Anesthetic Efficacy of Methoxyflurane Microdroplets in Man", Anesthesiology 67(3A):A254.
Knox et al., 2004, "New research shows intradermal rather than intramuscular vaccine injection could stretch flu vaccine supplies," National Public Radio: All Things Considered (Nov. 3, 2004).
Kohn, 2004, "Flu shot technique yields more doses, studies find; critics say injecting skin rather than muscle is too difficult for common use," The Baltimore Sun: Telegraph 3A (Nov. 4, 2004).
Leroy et al., 1984, "Pharmacokinetics of Ceftazidime in Normal and Uremic Subjects", Antimicrobal Agents and Chemotherapy 25(5):638-642.
Majeski et al., 2004, "Technique could stretch vaccine; changing the way shots are given means the current supply of flu vaccine could immunize 10 times as many people, two Minnesota physicians say" Saint Paul Pioneer Press: Main 1A (Oct. 27, 2004).
Majeski, 2004, "Alternate flu shot less effective in elderly; doctors proposed method to stretch vaccine supply," Saint Paul Pioneer Press: Main 17A (Nov. 4, 2004).
Marian et al., 2001, "Hypoglycemia activates compensatory mechanism of glucose metabolism of brain," Acta Biologica Hungarica 52(1):35-45.
McAllister et al., 1999, "Solid and Hollow Microneedles for Transdermal Protein Delivery," Proceed. Int'l. Symp. Control. Rel. Bioact. Mater. 26:192-193.
McAllister et al., 1999, "Thee-Dimensional Hollow Microneedle and Microtube Arrays," Conference: Solid-State Sensors and Actuators Transducers-Conference 12:1098-1103.
McElroy et al.. 1969, "Response to intradermal vaccination with A2, Hong Kong variant, influenza vaccine," N. Engl. J. Med. 281(19):1076.
McGugan et al., 1963, "Adrenal Suppression from Intradermal Triamcinolone", Journal of Investigative Dermatology 40:271-272.
Merriam-Webster's Collegiate Dictionary, 10th Edition, 1998, Merriam-Webster, Inc., Springfield, MA, p. 306.
MicroGroup's Stock Hypodermic Tubing Table.
Montagne et al., 2004, "Intradermal influenza vaccination—can less be more?" New England Journal of Medicine 351(22):2330-2332.
Niculescu et al., 1981, "Efficacy of an adsorbed trivalent split influenza vaccine administered by intradermal route," Arch. Roum. Path. Exp. Microbiol. 40(1):67-70.
Park, 1993, "Pharmacokinetics and Pharmacodynamics in the critically ill patient," Xenobiotica 23(11):1195-1230.
Payler, 1974, "Letter: Intradermal influenza vaccination," Br. Med. J. 2(921):727.
Payler, 1977, "Intradermal influenza vaccine using Portojet 1976," Br. Med. J. 2(6095):1152.
Pinski, 2000, p. 192 of "Soft tissue augmentation for the new millennium," Dermatological Therapy 13:192-197.
Product Brochure of Terumo Insulin Syringe (Oct. 6, 1990).
Puri et al., 2000, "An Investigation of the Intradermal Route as an Effective Means of Immunization for Microparticulate Vaccine Delivery Systems," Vaccine 18:2600-2612.
Rindfleisch et al., 2004, "La Crosse finding could curtail flu vaccine shortages," Wisconsin State Journal D9 (Nov. 14, 2004).
Scott et al., 1981, "Toxicity of Interferon," British Medical Journal 282:1345-1348.
Sebastien et al., 1998,"Microfabricated Needles: A Novel Approach to Transdermal Drug Delivery," Journal of Pharmaceutical Sciences 87(8):922-925.
Shute, 2004, "Second thoughts on the flu vaccine," Science & Society Public Health 137(17):80.
Smith, 2004, "Low-dose vaccine helps block flu, study says younger adults seen benefiting," The Boston Globe: National/Foreign A2 (Nov. 4, 2004).
Supersaxo et al., 1988, "Recombinant Human Interferon Alpha-2a: Delivery to Lymphoid Tissue by Selected Modes of Application," Pharmaceutical Research 5(8):472-476.
Sutherest, 1979, "Treatment of Pruritus Vulvae by Multiple Intradermal Injections of Alcohol. A Double-Blind Study," British Journal of Obstetrics and Gynecology 86:371-373.
Sveinsson, 1939, Investigation on the Influence of Insulin and Adrenalin in Rabbits with Alimentary Fatty Liver and Muscles and on the Content of Fat and Sugar in Blood:66-86.
Tauraso et al., 1969, "Effect of dosage and route of inoculation upon antigenicity of inactivated influenza virus vaccine (Hong Kong strain) in man," Bull. World Health Organ 41(3):507-516.
The American Heritage College Dictionary, 2000, 3rd Edition; Houghton Mifflin Company, Boston, New York, p. 368.
The Merck Manual of Diagnosis and Therapy (17th Ed.) 1999.
The Merck Manual of Diagnosis and Therapy, 1999, 17th Edition, Beers & Berkow, ed., Merck Research Laboratories, Division of Merck & Co., Inc., Whitehouse Station, NJ, pp. 2559-2567.
Tuft, 1931, "Active Immunization against Thyroid Fever, with Particular Reference to an Intradermal Method," Journal of Laboratory and Clinical Medicine:552-556.
Ward et al., 1975, "Pruritus Vulvae: Treatment by Multiple Intradermal Alcohol Injections," British Journal of Dermatology 93(2):201-204.
Written Opinion mailed by the International Searching Authority on Apr. 21, 2006 for PCT/US2004/014469, filed May 6, 2004.
Written Opinion mailed by the International Searching Authority on Dec. 14, 2006 for PCT/US2004/014033, filed May 6, 2004.
Written Opinion mailed by the International Searching Authority on Sep. 18, 2006 for PCT/US2005/016424, filed May 11, 2005.
Zaynoun et al., 1973, "The Effect of Intracutaneous Glucocorticoids on Plasma Cortisol Levels," British Journal of Dermatology 88(2):151-156.

\* cited by examiner

METHOD FOR ALTERING DRUG PHARMACOKINETICS BASED ON MEDICAL DELIVERY PLATFORM

CROSS REFERENCE TO RELATED APPLICATIONS

This application is a continuation of application Ser. No. 13/072,824, filed Mar. 28, 2011, which is a continuation of application Ser. No. 12/100,259, filed Apr. 9, 2008, which is a divisional of application Ser. No. 09/893,746, filed Jun. 29, 2001, which is a continuation-in-part of application Ser. No. 09/606,909, filed Jun. 29, 2000, each of which is hereby incorporated by reference in its entirety.

FIELD OF THE INVENTION

The present invention relates to methods and devices for administration of substances into the intradermal layer of skin.

BACKGROUND OF THE INVENTION

The importance of efficiently and safely administering pharmaceutical substances such as diagnostic agents and drugs has long been recognized. Although an important consideration for all pharmaceutical substances, obtaining adequate bioavailability of large molecules such as proteins that have arisen out of the biotechnology industry has recently highlighted this need to obtain efficient and reproducible absorption (Cleland et al., *Curr. Opin. Biotechnol.* 12: 212-219, 2001). The use of conventional needles has long provided one approach for delivering pharmaceutical substances to humans and animals by administration through the skin. Considerable effort has been made to achieve reproducible and efficacious delivery through the skin while improving the ease of injection and reducing patient apprehension and/or pain associated with conventional needles. Furthermore, certain delivery systems eliminate needles entirely, and rely upon chemical mediators or external driving forces such as iontophoretic currents or electroporation or thermal poration or sonophoresis to breach the stratum corneum, the outermost layer of the skin, and deliver substances through the surface of the skin. However, such delivery systems do not reproducibly breach the skin barriers or deliver the pharmaceutical substance to a given depth below the surface of the skin and consequently, clinical results can be variable. Thus, mechanical breach of the stratum corneum such as with needles, is believed to provide the most reproducible method of administration of substances through the surface of the skin, and to provide control and reliability in placement of administered substances.

Approaches for delivering substances beneath the surface of the skin have almost exclusively involved transdermal administration, i.e. delivery of substances through the skin to a site beneath the skin. Transdermal delivery includes subcutaneous, intramuscular or intravenous routes of administration of which, intramuscular (IM) and subcutaneous (SC) injections have been the most commonly used.

Anatomically, the outer surface of the body is made up of two major tissue layers, an outer epidermis and an underlying dermis, which together constitute the skin (for review, see *Physiology, Biochemistry, and Molecular Biology of the Skin, Second Edition*, L. A. Goldsmith, Ed., Oxford University Press, New York, 1991). The epidermis is subdivided into five layers or strata of a total thickness of between 75 and 150 µm. Beneath the epidermis lies the dermis, which contains two layers, an outermost portion referred to at the papillary dermis and a deeper layer referred to as the reticular dermis. The papillary dermis contains vast microcirculatory blood and lymphatic plexuses. In contrast, the reticular dermis is relatively acellular and avascular and made up of dense collagenous and elastic connective tissue. Beneath the epidermis and dermis is the subcutaneous tissue, also referred to as the hypodermis, which is composed of connective tissue and fatty tissue. Muscle tissue lies beneath the subcutaneous tissue.

As noted above, both the subcutaneous tissue and muscle tissue have been commonly used as sites for administration of pharmaceutical substances. The dermis, however, has rarely been targeted as a site for administration of substances, and this may be due, at least in part, to the difficulty of precise needle placement into the intradermal space. Furthermore, even though the dermis, in particular, the papillary dermis has been known to have a high degree of vascularity, it has not heretofore been appreciated that one could take advantage of this high degree of vascularity to obtain an improved absorption profile for administered substances compared to subcutaneous administration. This is because small drug molecules are typically rapidly absorbed after administration into the subcutaneous tissue which has been far more easily and predictably targeted than the dermis has been. On the other hand, large molecules such as proteins are typically not well absorbed through the capillary epithelium regardless of the degree of vascularity so that one would not have expected to achieve a significant absorption advantage over subcutaneous administration by the more difficult to achieve intradermal administration even for large molecules.

One approach to administration beneath the surface to the skin and into the region of the intradermal space has been routinely used in the Mantoux tuberculin test. In this procedure, a purified protein derivative is injected at a shallow angle to the skin surface using a 27 or 30 gauge needle (Flynn et al, *Chest* 106: 1463-5, 1994). A degree of uncertainty in placement of the injection can, however, result in some false negative test results. Moreover, the test has involved a localized injection to elicit a response at the site of injection and the Mantoux approach has not led to the use of intradermal injection for systemic administration of substances.

Some groups have reported on systemic administration by what has been characterized as "intradermal" injection. In one such report, a comparison study of subcutaneous and what was described as "intradermal" injection was performed (Autret et al, *Therapie* 46:5-8, 1991). The pharmaceutical substance tested was calcitonin, a protein of a molecular weight of about 3600. Although it was stated that the drug was injected intradermally, the injections used a 4 mm needle pushed up to the base at an angle of 60. This would have resulted in placement of the injectate at a depth of about 3.5 mm and into the lower portion of the reticular dermis or into the subcutaneous tissue rather than into the vascularized papillary dermis. If, in fact, this group injected into the lower portion of the reticular dermis rather than into the subcutaneous tissue, it would be expected that the substance would either be slowly absorbed in the relatively less vascular reticular dermis or diffuse into the subcutaneous region to result in what would be functionally the same as subcutaneous administration and absorption. Such actual or functional subcutaneous administration would explain the reported lack of difference between subcutaneous and what was characterized as intradermal administration, in the times at which maximum plasma concentration was reached, the concentrations at each assay time and the areas under the curves.

Similarly, Bressolle et al. administered sodium ceftazidime in what was characterized as "intradermal" injection using a 4 mm needle (Bressolle et al. *J. Pharm. Sci.* 82:1175-1178, 1993). This would have resulted in injection to a depth of 4 mm below the skin surface to produce actual or functional subcutaneous injection, although good subcutaneous absorption would have been anticipated in this instance because sodium ceftazidime is hydrophilic and of relatively low molecular weight.

Another group reported on what was described as an intradermal drug delivery device (U.S. Pat. No. 5,007,501). Injection was indicated to be at a slow rate and the injection site was intended to be in some region below the epidermis, i.e., the interface between the epidermis and the dermis or the interior of the dermis or subcutaneous tissue. This reference, however, provided no teachings that would suggest a selective administration into the dermis nor did the reference suggest any possible pharmacokinetic advantage that might result from such selective administration.

Thus there remains a continuing need for efficient and safe methods and devices for administration of pharmaceutical substances.

SUMMARY OF THE INVENTION

The present disclosure relates to a new parenteral administration method based on directly targeting the dermal space whereby such method dramatically alters the pharmacokinetics (PK) and pharmacodynamics (PD) parameters of administered substances. By the use of direct intradermal (ID) administration means hereafter referred to as dermal-access means, for example, using microneedle-based injection and infusion systems (or other means to accurately target the intradermal space), the pharmacokinetics of many substances including drugs and diagnostic substances, which are especially protein and peptide hormones, can be altered when compared to traditional parental administration routes of subcutaneous and intravenous delivery. These findings are pertinent not only to microdevice-based injection means, but other delivery methods such as needless or needle-free ballistic injection of fluids or powders into the ID space, Mantoux-type ID injection, enhanced iontophoresis through microdevices, and direct deposition of fluid, solids, or other dosing forms into the skin. Disclosed is a method to increase the rate of uptake for parenterally-administered drugs without necessitating IV access. One significant beneficial effect of this delivery method is providing a shorter $T_{max}$. (time to achieve maximum blood concentration of the drug). Potential corollary benefits include higher maximum concentrations for a given unit dose ($C_{max}$), higher bioavailability, more rapid uptake rates, more rapid onset of pharmacodynamics or biological effects, and reduced drug depot effects. According to the present invention, improved pharmacokinetics means increased bioavailability, decreased lag time ($T_{lag}$), decreased $T_{max}$, more rapid absorption rates, more rapid onset and/or increased $C_{max}$ for a given amount of compound administered, compared to subcutaneous, intramuscular or other non-IV parenteral means of drug delivery.

By bioavailability is meant the total amount of a given dosage that reached the blood compartment. This is generally measured as the area under the curve in a plot of concentration vs. time. By "lag time" is meant the delay between the administration of a compound and time to measurable or detectable blood or plasma levels. $T_{max}$ is a value representing the time to achieve maximal blood concentration of the compound, and $C_{max}$ is the maximum blood concentration reached with a given dose and administration method. The time for onset is a function of $T_{lag}$, $T_{max}$ and $C_{max}$, as all of these parameters influence the time necessary to achieve a blood (or target tissue) concentration necessary to realize a biological effect. $T_{max}$ and $C_{max}$ can be determined by visual inspection of graphical results and can often provide sufficient information to compare two methods of administration of a compound. However, numerical values can be determined more precisely by analysis using kinetic models (as described below) and/or other means known to those of skill in the art.

Directly targeting the dermal space as taught by the invention provides more rapid onset of effects of drugs and diagnostic substances. The inventors have found that substances can be rapidly absorbed and systemically distributed via controlled ID administration that selectively accesses the dermal vascular and lymphatic microcapillaries, thus the substances may exert their beneficial effects more rapidly than SC administration. This has special significance for drugs requiring rapid onset, such as insulin to decrease blood glucose, pain relief such as for breakthrough cancer pain, or migraine relief, or emergency rescue drugs such as adrenaline or antivenom. Natural hormones are also released in pulsatile fashion with a rapid onset burst followed by rapid clearance. Examples include insulin that is released in response to biological stimulus, for example high glucose levels. Another example is female reproductive hormones, which are released at time intervals in pulsatile fashion. Human growth hormone is also released in normal patients in a pulsatile fashion during sleep. This benefit allows better therapy by mimicking the natural body rhythms with synthetic drug compounds. Likewise, it may better facilitate some current therapies such as blood glucose control via insulin delivery. Many current attempts at preparing "closed loop" insulin pumps are hindered by the delay period between administering the insulin and waiting for the biological effect to occur. This makes it difficult to ascertain in real-time whether sufficient insulin has been given, without overtitrating and risking hypoglycemia. The more rapid PK/PD of ID delivery eliminates much of this type of problem.

Mammalian skin contains two layers, as discussed above, specifically, the epidermis and dermis. The epidermis is made up of five layers, the stratum corneum, the stratum lucidum, the stratum granulosum, the stratum spinosum and the stratum germinativum and the dermis is made up of two layers, the upper papillary dermis and the deeper reticular dermis. The thickness of the dermis and epidermis varies from individual to individual, and within an individual, at different locations on the body. For example, it has been reported that the epidermis varies in thickness from about 40 to about 90 μm and the dermis varies in thickness ranging from just below the epidermis to a depth of from less than 1 mm in some regions of the body to just under 2 to about 4 mm in other regions of the body depending upon the particular study report (Hwang et al., *Ann Plastic Surg* 46:327-331, 2001; Southwood, *Plast. Reconstr. Surg* 15:423-429, 1955; Rushmer et al., *Science* 154:343-348, 1966).

As used herein, intradermal is intended to mean administration of a substance into the dermis in such a manner that the substance readily reaches the richly vascularized papillary dermis and is rapidly absorbed into the blood capillaries and/or lymphatic vessels to become systemically bioavailable. Such can result from placement of the substance in the upper region of the dermis, i.e. the papillary dermis or in the upper portion of the relatively less vascular reticular dermis such that the substance readily diffuses into the papillary dermis. It is believed that placement of a substance predominately at a depth of at least about 0.3 mm, more preferably, at least about 0.4 mm and most preferably at least about 0.5 mm up to a depth of no more than about 2.5 mm, more preferably, no more than about 2.0 mm and most preferably no more than about 1.7 mm will result in rapid absorption of macromolecular and/or hydrophobic substances. Placement of the substance predominately at greater depths and/or into the lower portion of the reticular dermis is believed to result in the substance being slowly absorbed in the less vascular reticular dermis or in the subcutaneous region either of which would result in reduced absorption of macromolecular and/or hydrophobic substances. The controlled delivery of a substance in this dermal space below the papillary dermis in the reticular dermis, but sufficiently above the interface between the dermis and the subcutaneous tissue, should enable an efficient (outward) migration of the substance to the (undisturbed) vascular and lymphatic microcapillary bed (in the papillary dermis), where it can be absorbed into systemic circulation via these microcapillaries without being sequestered in transit by any other cutaneous tissue compartment.

Another benefit of the invention is to achieve more rapid systemic distribution and offset of drugs or diagnostic agents. This is also pertinent for many hormones that in the body are secreted in a pulsatile fashion. Many side effects are associated with having continuous circulating levels of substances administered. A very pertinent example is female reproductive hormones that actually have the opposite effect (cause infertility) when continuously present in the blood. Likewise, continuous and elevated levels of insulin are suspected to down regulate insulin receptors both in quantity and sensitivity.

Another benefit of the invention is to achieve higher bioavailabilities of drugs or diagnostic agents. This effect has been most dramatic for ID administration of high molecular weight substances, especially proteins, peptides, and polysaccharides. The direct benefit is that ID administration with enhanced bioavailability, allows equivalent biological effects while using less active agent. This results in direct economic benefit to the drug manufacturer and perhaps consumer, especially for expensive protein therapeutics and diagnostics. Likewise, higher bioavailability may allow reduced overall dosing and decrease the patient's side effects associated with higher dosing.

Another benefit of the invention is the attainment of higher maximum concentrations of drugs or diagnostic substances. The inventors have found that substances administered ID are absorbed more rapidly, with bolus administration resulting in higher initial concentrations. This is most beneficial for substances whose efficacy is related to maximal concentration. The more rapid onset allows higher $C_{Max}$ values to be reached with lesser amounts of the substance. Therefore, the dose can be reduced, providing an economic benefit, as well as a physiological benefit since lesser amounts of the drug or diagnostic agent has to be cleared by the body.

Another benefit of the invention is no change in systemic elimination rates or intrinsic clearance mechanisms of drugs or diagnostic agents. All studies to date by the applicants have maintained the same systemic elimination rate for the substances tested as via IV or SC dosing routes. This indicates this dosing route has no change in the biological mechanism for systemic clearance. This is an advantageous from a regulatory standpoint, since degradation and clearance pathways need not be reinvestigated prior to filing for FDA approval. This is also beneficial from a pharmacokinetics standpoint, since it allows predictability of dosing regimes. Some substances may be eliminated from the body more rapidly if their clearance mechanism are concentration dependent. Since ID delivery results in higher Cmax, clearance rate may be increased, although the intrinsic mechanism remains unchanged.

Another benefit of the invention is no change in pharmacodynamic mechanism or biological response mechanism. As stated above, administered drugs by the methods taught by the applicants still exert their effects by the same biological pathways that are intrinsic to other delivery means. Any pharmacodynamic changes are related only to the difference patterns of appearance, disappearance, and drug or diagnostic agent concentrations present in the biological system.

Using the methods of the present invention, pharmaceutical compounds may be administered as a bolus, or by infusion. As used herein, the term "bolus" is intended to mean an amount that is delivered within a time period of less than ten (10) minutes. "Infusion" is intended to mean the delivery of a substance over a time period greater than ten (10) minutes. It is understood that bolus administration or delivery can be carried out with rate controlling means, for example a pump, or have no specific rate controlling means, for example user self-injection.

Another benefit of the invention is removal of the physical or kinetic barriers invoked when drugs passes through and becomes trapped in cutaneous tissue compartments prior to systemic absorption. Elimination of such barriers leads to an extremely broad applicability to various drug classes. Many drugs administered subcutaneously exert this depot effect—that is, the drug is slowly released from the SC space, in which it is trapped, as the rate determining step prior to systemic absorption, due to affinity for or slow diffusion through the fatty adipose tissue. This depot effect results in a lower $C_{max}$ and longer $T_{max}$, compared to ID, and can result in high inter-individual variability of absorption. This effect is also pertinent for comparison to transdermal delivery methods including passive patch technology, with or without permeation enhances, iontophoretic technology, sonopheresis, or stratum corneum ablation or disruptive methods. Transdermal patch technology relies on drug partitioning through the highly impermeable stratum corneum and epidermal barriers. Few drugs except highly lipophilic compounds can breach this barrier, and those that do, often exhibit extended offset kinetics due to tissue saturation and entrappment of the drugs. Active transdermal means, while often faster than passive transfer means, are still restricted to compound classes that can be moved by charge repulsion or other electronic or electrostatic means, or carried passively through the transient pores caused by cavitation of the tissue during application of sound waves. The stratum corneum and epidermis still provide effective means for inhibiting this transport. Stratum corneum removal by thermal or laser ablation, abrasive means or otherwise, still lacks a driving force to facilitate penetration or uptake of drugs. Direct ID administration by mechanical means overcomes the kinetic barrier properties of skin, and is not limited by the pharmaceutical or physicochemical properties of the drug or its formulation excipients.

Another benefit of the invention is highly controllable dosing regimens. The applicants have determined that ID infusion studies have demonstrated dosing profiles that are highly controllable and predictable due to the rapid onset and offset kinetics of drugs or diagnostic agents delivered by this route. This allows almost absolute control over the desired dosing regimen when ID delivery is coupled with a fluid control means or other control system to regulate metering of the drug or diagnostic agent into the body. This single benefit alone is one of the principal goals of most drug or diagnostic agent delivery methods. Bolus ID substance administration as defined previously results in kinetics most similar to IV injection and is most desirable for pain relieving compounds, mealtime insulin, rescue drugs, erectile dysfunction compounds, or other drugs that require rapid onset. Also included would be combinations of substances capable of acting alone or synergistically. Extending the ID administration duration via infusion can effectively mimic SC uptake parameters, but with better predictability. This profile is particularly good for substances such as growth hormones, or analgesics. Longer duration infusion, typically at lower infusion rates can result in continuous low basal levels of drugs that is desired for anticoagulants, basal insulin, and chronic pain therapy. These kinetic profiles can be combined in multiple fashion to exhibit almost any kinetic profile desired. An example would be to pulsatile delivery of fertility hormone (LHRH) for pregnancy induction, which requires intermittent peaks every 90 minutes with total clearance between pulses. Other examples would be rapid peak onset of drugs for migraine relief, followed by lower levels for pain prophylaxis.

Another benefit of the invention is reduced degradation of drugs and diagnostic agents and/or undesirable immunogenic activity. Transdermal methods using chemical enhancers or iontophoresis, or sonophoresis or electroporation or thermal poration require that a drug pass through the viable epidermal layer, which has high metabolic and immunogenic activity. Metabolic conversion of substances in the epidermis or sequestration by immunoglobulins reduces the amount of drug available for absorption. The ID administration circumvents this problem by placing the drug directly in the dermis, thus bypassing the epidermis entirely.

These and other benefits of the invention are achieved by directly targeting absorption by the papillary dermis and by controlled delivery of drugs, diagnostic agents, and other substances to the dermal space of skin. The inventors have found that by specifically targeting the intradermal space and controlling the rate and pattern of delivery, the pharmacokinetics exhibited by specific drugs can be unexpectedly improved, and can in many situations be varied with resulting clinical advantage. Such pharmacokenetics cannot be as readily obtained or controlled by other parenteral administration routes, except by IV access.

The present invention improves the clinical utility of ID delivery of drugs, diagnostic agents, and other substances to humans or animals. The methods employ dermal-access means (for example a small gauge needle, especially microneedles), to directly target the intradermal space and to deliver substances to the intradermal space as a bolus or by infusion. It has been discovered that the placement of the dermal-access means within the dermis provides for efficacious delivery and pharmacokinetic control of active substances. The dermal-access means is so designed as to prevent leakage of the substance from the skin and improve adsorption within the intradermal space. The pharmacokinetics of hormone drugs delivered according to the methods of the invention have been found to be vastly different to the pharmacokinetics of conventional SC delivery of the drug, indicating that ID administration according to the methods of the invention will provide improved clinical results. Delivery devices that place the dermal-access means at an appropriate depth in the intradermal space and control the volume and rate of fluid delivery provide accurate delivery of the substance to the desired location without leakage.

Disclosed is a method to increase the rate of uptake for parenterally-administered drugs without necessitating IV access. This effect provides a shorter $T_{max}$. Potential corollary benefits include higher maximum concentrations for a given unit dose ($C_{max}$), higher bioavailability, more rapid onset of pharmacodynamics or biological effects, and reduced drug depot effects.

It has also been found that by appropriate depth control of the dermal-access means within the intradermal space that the pharmacokinetics of hormone drugs delivered according to the methods of the invention can, if required, produce similar clinical results to that of conventional SC delivery of the drug.

The pharmacokinetic profile for individual compounds will vary according to the chemical properties of the compounds. For example, compounds that are relatively large, having a molecular weight of at least 1000 Daltons as well as larger compounds of at least 2000 Daltons, at least 4000 Daltons, at least 10,000 Daltons and larger and/or hydrophobic compounds are expected to show the most significant changes compared to traditional parenteral methods of administration, such as intramuscular, subcutaneous or subdermal injection. It is expected that small hydrophilic substances, on the whole, will exhibit similar kinetics for ID delivery compared to other methods.

DETAILED DESCRIPTION OF THE INVENTION

Figure 1:
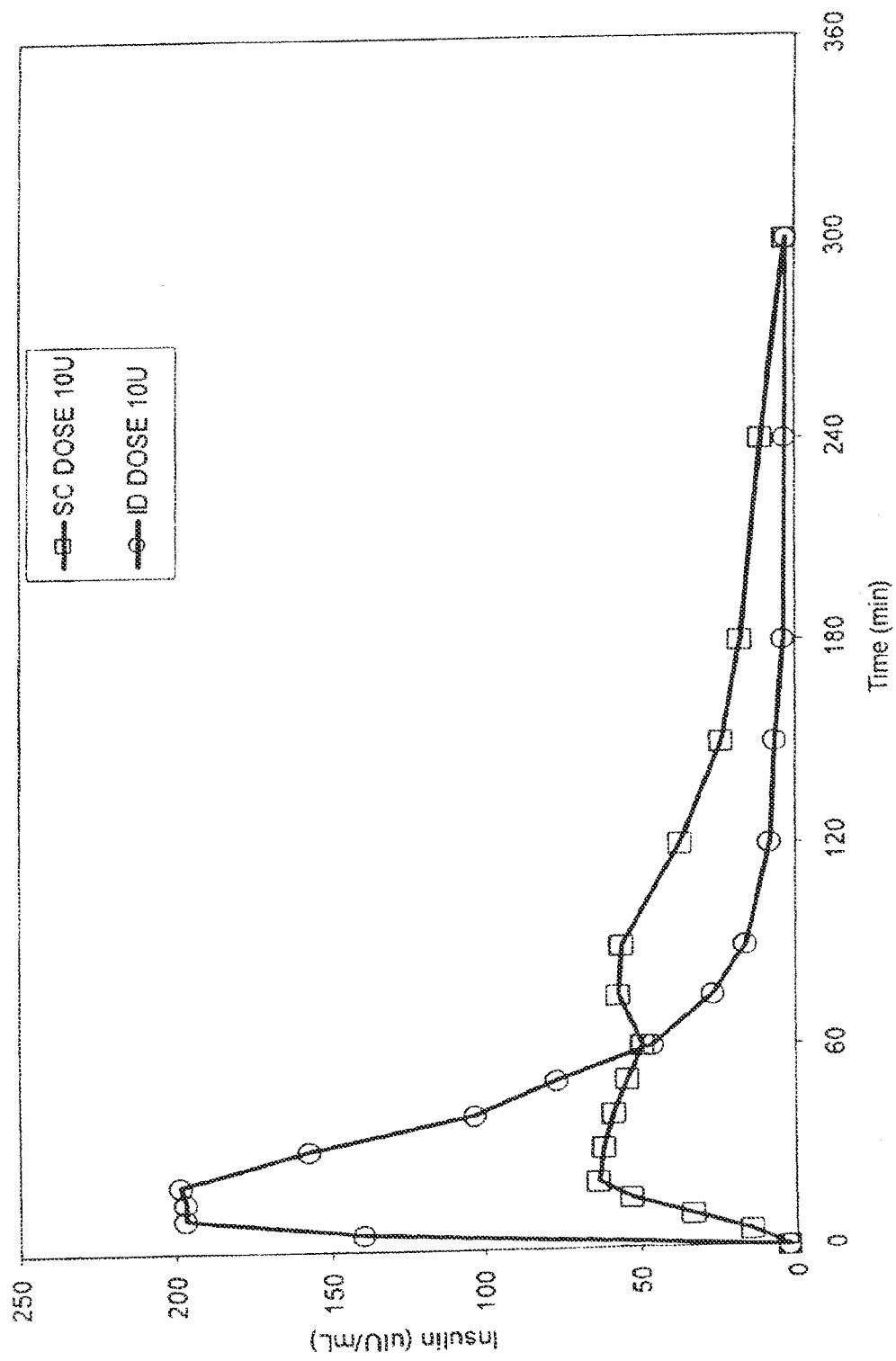
FIG. 1 shows a time course of plasma insulin levels of intradermal versus subcutaneous bolus administration of fast-acting.

The present invention provides a method for therapeutic treatment by delivery of a drug or other substance to a human or animal subject by directly targeting the intradermal space, where the drug or substance is administered to the intradermal space through one or more dermal-access means incorporated within the device. Substances infused according to the methods of the invention have been found to exhibit pharmacokinetics superior to, and more clinically desirable than that observed for the same substance administered by SC injection.

The dermal-access means used for ID administration according to the invention is not critical as long as it penetrates the skin of a subject to the desired targeted depth within the intradermal space without passing through it. In most cases, the device will penetrate the skin and to a depth of about 0.5-2 mm. The dermal-access means may comprise conventional injection needles, catheters or microneedles of all known types, employed singularly or in multiple needle arrays. The dermal-access means may comprise needleless devices including ballistic injection devices. The terms "needle" and "needles" as used herein are intended to encompass all such needle-like structures. The term microneedles as used herein are intended to encompass structures smaller than about 30 gauge, typically about 31-50 gauge when such structures are cylindrical in nature. Non-cylindrical structures encompass by the term microneedles would therefore be of comparable diameter and include pyramidal, rectangular, octagonal, wedged, and other geometrical shapes. Dermal-access means also include ballistic fluid injection devices, powder-jet delivery devices, piezoelectric, electromotive, electromagnetic assisted delivery devices, gas-assisted delivery devices, of which directly penetrate the skin to provide access for delivery or directly deliver substances to the targeted location within the dermal space. By varying the targeted depth of delivery of substances by the dermal-access means, pharmacokinetic and pharmacodynamic (PK/PD) behavior of the drug or substance can be tailored to the desired clinical application most appropriate for a particular patient's condition. The targeted depth of delivery of substances by the dermal-access means may be controlled manually by the practitioner, or with or without the assistance of indicator means to indicate when the desired depth is reached. Preferably however, the device has structural means for controlling skin penetration to the desired depth within the intradermal space. This is most typically accomplished by means of a widened area or hub associated with the shaft of the dermal-access means that may take the form of a backing structure or platform to which the needles are attached. The length of microneedles as dermal-access means are easily varied during the fabrication process and are routinely produced in less than 2 mm length. Microneedles are also a very sharp and of a very small gauge, to further reduce pain and other sensation during the injection or infusion. They may be used in the invention as individual single-lumen microneedles or multiple microneedles may be assembled or fabricated in linear arrays or two-dimensional arrays as to increase the rate of delivery or the amount of substance delivered in a given period of time. Microneedles may be incorporated into a variety of devices such as holders and housings that may also serve to limit the depth of penetration. The dermal-access means of the invention may also incorporate reservoirs to contain the substance prior to delivery or pumps or other means for delivering the drug or other substance under pressure. Alternatively, the device housing the dermal-access means may be linked externally to such additional components.

IV-like pharmacokinetics is accomplished by administering drugs into the dermal compartment in intimate contact with the capillary microvasculature and lymphatic microvasculature. In should be understood that the terms microcapillaries or capillary beds refer to either vascular or lymphatic drainage pathways within the dermal area.

While not intending to be bound by any theoretical mechanism of action, it is believed that the rapid absorption observed upon administration into the dermis is achieved as a result of the rich plexuses of blood and lymphatic vessels in the dermis. However, the presence of blood and lymphatic plexuses in the dermis would not by itself be expected to produce an enhanced absorption of macromolecules. This is because capillary endothelium is normally of low permeability or impermeable to macromolecules such as proteins, polysaccharides, nucleic acid polymers, substance having polymers attached such as pegylated proteins and the like. Such macromolecules have a molecular weight of at least 1000 Daltons or of a higher molecular weight of at least, 2000 Daltons, at least 4000 Daltons, at least 10,000 Daltons or even higher. Furthermore, a relatively slow lymphatic drainage from the interstitium into the vascular compartment would also not be expected to produce a rapid increase in plasma concentration upon placement of a pharmaceutical substance into the dermis.

One possible explanation for the unexpected enhanced absorption reported herein is that upon injection of substances so that they readily reach the papillary dermis an increase in blood flow and capillary permeability results. For example, it is known that a pinprick insertion to a depth of 3 mm produces an increase in blood flow and this has been postulated to be independent of pain stimulus and due to tissue release of histamine (Arildsson et al., *Microvascular Res.* 59:122-130, 2000). This is consistent with the observation that an acute inflammatory response elicited in response to skin injury produces a transient increase in blood flow and capillary permeability (see *Physiology, Biochemistry, and Molecular Biology of the Skin, Second Edition*, L. A. Goldsmith, Ed., Oxford Univ. Press, New York, 1991, p. 1060; Wilhem, *Rev. Can. Biol.* 30:153-172, 1971). At the same time, the injection into the intradermal layer would be expected to increase interstitial pressure. It is known that increasing interstitial pressure from values (beyond the "normal range") of about −7 to about +2 mmHg distends lymphatic vessels and increases lymph flow (Skobe et al., *J. Investig. Dermatol. Symp. Proc.* 5:14-19, 2000). Thus, the increased interstitial pressure elicited by injection into the intradermal layer is believed to elicit increased lymph flow and increased absorption of substances injected into the dermis.

By "improved pharmacokinetics" it is meant that an enhancement of pharmacokinetic profile is achieved as measured, for example, by standard pharmacokinetic parameters such as time to maximal plasma concentration ($T_{max}$), the magnitude of maximal plasma concentration ($C_{max}$) or the time to elicit a minimally detectable blood or plasma concentration ($T_{lag}$). By enhanced absorption profile, it is meant that absorption is improved or greater as measured by such pharmacokinetic parameters. The measurement of pharmacokinetic parameters and determination of minimally effective concentrations are routinely performed in the art. Values obtained are deemed to be enhanced by comparison with a standard route of administration such as, for example, subcutaneous administration or intramuscular administration. In such comparisons, it is preferable, although not necessarily essential, that administration into the intradermal layer and administration into the reference site such as subcutaneous administration involve the same dose levels, i.e. the same amount and concentration of drug as well as the same carrier vehicle and the same rate of administration in terms of amount and volume per unit time. Thus, for example, administration of a given pharmaceutical substance into the dermis at a concentration such as 100 μg/ml and rate of 100 μL per minute over a period of 5 minutes would, preferably, be compared to administration of the same pharmaceutical substance into the subcutaneous space at the same concentration of 100 μg/ml and rate of 100 μL per minute over a period of 5 minutes.

The enhanced absorption profile is believed to be particularly evident for substances which are not well absorbed when injected subcutaneously such as, for example, macromolecules and/or hydrophobic substances. Macromolecules are, in general, not well absorbed subcutaneously and this may be due, not only to their size relative to the capillary pore size, it may also be due to their slow diffusion through the interstitium because of their size. It is understood that macromolecules can possess discrete domains having a hydrophobic and/or hydrophilic nature. In contrast, small molecules which are hydrophilic are generally well absorbed when administered subcutaneously and it is possible that no enhanced absorption profile would be seen upon injection into the dermis compared to absorption following subcutaneous administration. Reference to hydrophobic substances herein is intended to mean low molecular weight substances, for example substances with molecular weights less than 1000 Daltons, which have a water solubility which is low to substantially insoluble.

The above-mentioned PK and PD benefits are best realized by accurate direct targeting of the dermal capillary beds. This is accomplished, for example, by using microneedle systems of less than about 250 micron outer diameter, and less than 2 mm exposed length. Such systems can be constructed using known methods of various materials including steel, silicon, ceramic, and other metals, plastic, polymers, sugars, biological and or biodegradable materials, and/or combinations thereof.

It has been found that certain features of the intradermal administration methods provide clinically useful PK/PD and dose accuracy. For example, it has been found that placement of the needle outlet within the skin significantly affects PK/PD parameters. The outlet of a conventional or standard gauge needle with a bevel has a relatively large exposed height (the vertical rise of the outlet). Although the needle tip may be placed at the desired depth within the intradermal space, the large exposed height of the needle outlet causes the delivered substance to be deposited at a much shallower depth nearer to the skin surface. As a result, the substance tends to effuse out of the skin due to backpressure exerted by the skin itself and to pressure built up from accumulating fluid from the injection or infusion. That is, at a greater depth a needle outlet with a greater exposed height will still seal efficiently where as an outlet with the same exposed height will not seal efficiently when placed in a shallower depth within the intradermal space. Typically, the exposed height of the needle outlet will be from 0 to about 1 mm. A needle outlet with an exposed height of 0 mm has no bevel and is at the tip of the needle. In this case, the depth of the outlet is the same as the depth of penetration of the needle. A needle outlet that is either formed by a bevel or by an opening through the side of the needle has a measurable exposed height. It is understood that a single needle may have more than one opening or outlets suitable for delivery of substances to the dermal space.

It has also been found that by controlling the pressure of injection or infusion may avoid the high backpressure exerted during ID administration. By placing a constant pressure directly on the liquid interface a more constant delivery rate can be achieved, which may optimize absorption and obtain the improved pharmacokinetics. Delivery rate and volume can also be controlled to prevent the formation of wheals at the site of delivery and to prevent backpressure from pushing the dermal-access means out of the skin. The appropriate delivery rates and volumes to obtain these effects for a selected substance may be determined experimentally using only ordinary skill. Increased spacing between multiple needles allows broader fluid distribution and increased rates of delivery or larger fluid volumes. In addition, it has been found that ID infusion or injection often produces higher initial plasma levels of drug than conventional SC administration, particularly for drugs that are susceptible to in vivo degradation or clearance or for compounds that have an affinity to the SC adipose tissue or for macromolecules that diffuse slowly through the SC matrix. This may, in many cases, allow for smaller doses of the substance to be administered via the ID route.

The administration methods useful for carrying out the invention include both bolus and infusion delivery of drugs and other substances to humans or animals subjects. A bolus dose is a single dose delivered in a single volume unit over a relatively brief period of time, typically less than about 10 minutes. Infusion administration comprises administering a fluid at a selected rate that may be constant or variable, over a relatively more extended time period, typically greater than about 10 minutes. To deliver a substance the dermal-access means is placed adjacent to the skin of a subject providing directly targeted access within the intradermal space and the substance or substances are delivered or administered into the intradermal space where they can act locally or be absorbed by the bloodstream and be distributed systematically. The dermal-access means may be connected to a reservoir containing the substance or substances to be delivered. The form of the substance or substances to be delivered or administered include solutions thereof in pharmaceutically acceptable diluents or solvents, emulsions, suspensions, gels, particulates such as micro- and nanoparticles either suspended or dispersed, as well as in-situ forming vehicles of the same. Delivery from the reservoir into the intradermal space may occur either passively, without application of the external pressure or other driving means to the substance or substances to be delivered, and/or actively, with the application of pressure or other driving means. Examples of preferred pressure generating means include pumps, syringes, elastomer membranes, gas pressure, piezoelectric, electromotive, electromagnetic pumping, or Belleville springs or washers or combinations thereof. If desired, the rate of delivery of the substance may be variably controlled by the pressure-generating means. As a result, the substance enters the intradermal space and is absorbed in an amount and at a rate sufficient to produce a clinically efficacious result.

As used herein, the term "clinically efficacious result" is meant a clinically useful biological response including both diagnostically and therapeutically useful responses, resulting from administration of a substance or substances. For example, diagnostic testing or prevention or treatment of a disease or condition is a clinically efficacious result. Such clinically efficacious results include diagnostic results such as the measurement of glomerular filtration pressure following injection of inulin, the diagnosis of adrenocortical function in children following injection of ACTH, the causing of the gallbladder to contract and evacuate bile upon injection of cholecystokinin and the like as well as therapeutic results, such as clinically adequate control of blood sugar levels upon injection of insulin, clinically adequate management of hormone deficiency following hormone injection such as parathyroid hormone or growth hormone, clinically adequate treatment of toxicity upon injection of an antitoxin and the like.

Substances that can be delivered intradermally in accordance with the present invention are intended to include pharmaceutically or biologically active substances including include diagnostic agents, drugs, and other substances which provide therapeutic or health benefits such as for example nutraceuticals. Diagnostic substances useful with the present invention include macromolecular substances such as, for example, inulin, ACTH (e.g. corticotropin injection), luteinizing hormone-releasing hormone (e.g., Gonadorelin Hydrochloride), growth hormone-releasing hormone (e.g. Sermorelin Acetate), cholecystokinin (Sincalide), parathyroid hormone and fragments thereof (e.g. Teriparatide Acetate), thyroid releasing hormone and analogs thereof (e.g. protirelin), secretin and the like.

Therapeutic substances which can be used with the present invention include Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as Hirulog, IgE suppressors, Insulin, insulinotropin and analogs, Insulin-like growth factors, Interferons, Interleukins, Luteinizing hormone, Luteinizing hormone releasing hormone and analogs, Heparins, Low molecular weight heparins and other natural, modified, or synthetic glycoaminoglycans, M-CSF, metoclopramide, Midazolam, Monoclonal antibodies, Peglyated antibodies, Pegylated proteins or any proteins modified with hydrophilic or hydrophobic polymers or additional functional groups, Fusion proteins, Single chain antibody fragments or the same with any combination of attached proteins, macromolecules, or additional functional groups thereof, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, *rubella*, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, *chlamydia*, non-typeable haemophilus, *moraxella catarrhalis*, human papilloma virus, tuberculosis including BCG, gonorrhoea, asthma, atteroschlerosis malaria, *E-coli*, Alzheimer's Disease, *H. Pylori*, salmonella, diabetes, cancer, herpes simplex, human papilloma and the like other substances including all of the major therapeutics such as agents for the common cold, Anti-addiction, anti-allergy, anti-emetics, anti-obesity, anti-osteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, and sexual hypofunction and tranquilizers.

Pharmacokinetic analysis of insulin infusion data was carried out as follows. Stepwise nonlinear least-squares regression was used to analyze the insulin concentration-time data from each individual animal. Initially, an empirical biexponential equation was fit to the insulin concentration-time data for the negative control condition. This analysis assumed first-order release of residual insulin, and recovered parameters for the first-order rate constant for release, the residual insulin concentration at the release site, a lag time for release, and a first-order rate constant for elimination of insulin from the systemic circulation. The parameters recovered in this phase of the analysis are of no intrinsic importance, but merely account for the fraction of circulating insulin derived from endogenous sources.

The second step of the analysis involved fitting an explicit compartmental model to the insulin concentration-time data during and after subcutaneous or intradermal infusion. The scheme upon which the mathematical model was based is shown in the upper part of FIG. 1. [PK/PD model fig]. Infusion of insulin proceeded from t=0 to t=240 min; after a lag time ($t_{lag,2}$), absorption from the infusion site was mediated by a first-order process governed by the absorption rate constant $k_a$. Insulin absorbed into the systemic circulation distributed into an apparent volume V contaminated by an unknown fractional bioavailability F, and was eliminated according to a first-order rate constant K. The fitting routine recovered estimates of $t_{lag,2}$, $k_a$, V/F, and K; parameters associated with the disposition of endogenous insulin ($C_R$, $t_{lag,2}$, $k_R$), which were recovered in the first step of the analysis, were treated as constants.

Parameter estimates are reported as mean±SD. The significance of differences in specific parameters between the two different modes of insulin administration (subcutaneous versus intradermal infusion) was assessed with the paired Student's t-test.

Pharmacodynamic analysis of insulin infusion data was calculated as follows. Plasma concentrations of glucose were used as a surrogate for the pharmacological effect of insulin. The change in response variable R (plasma glucose concentration) with respect to time t was modeled as $$\frac{dR}{dt} = k_{in} - E \cdot k_{out}$$

where $k_{in}$ is the zero-order infusion of glucose, $o_{ut}$ is the first-order rate constant mediating glucose elimination, and E is the effect of insulin according to the sigmoid Hill relationship $$E = \frac{E_{max} \cdot C^\gamma}{EC_{50}^\gamma + C^\gamma}$$

in which $M_{ax}$ is the maximal stimulation of $o_{ut}$ by insulin, $EC_{50}$ is the insulin concentration at which stimulation of $o_{ut}$ is half maximal, C is the concentration of insulin, and $\gamma$ is the Hill coefficient of the relationship. Initial modeling efforts utilized the plasma concentration of insulin as the mediator of pharmacological response. However, this approach did not capture the delay in response of plasma glucose to increasing concentrations of plasma insulin. Therefore, an effect-compartment modeling approach was finally adopted in which the effect of insulin was mediated from a hypothetical effect compartment peripheral to the systemic pharmacokinetic compartment.

The pharmacodynamic analysis was conducted in two steps. In the first step of the analysis, initial estimates of the pharmacokinetic parameters associated with the disposition of glucose ($o_{ut}$ and the volume of distribution of glucose, $V_{glucose}$) were determined from the glucose concentration-time data in the negative control condition. The full integrated pharmacokinetic-pharmacodynamic model then was fit simultaneously to the glucose concentration-time data from the negative control condition and each insulin delivery condition for each animal (i.e., two sets of pharmacodynamic parameters were obtained for each animal: one from the simultaneous analysis of the subcutaneous insulin infusion/negative control data, and one from the simultaneous analysis of the intradermal insulin infusion/negative control data). In all pharmacodynamic analyses, the parameters governing insulin disposition obtained during pharmacokinetic analysis of insulin concentration-time data from each animal were held constant.

All other pharmacokinetic analyses were calculated using non-compartmental methods using similar software programs and techniques known in the art.

Having described the invention in general, the following specific but not limiting examples and reference to the accompanying Figures set forth various examples for practicing the dermal accessing, direct targeting drug administration method and examples of dermal administered drug substances providing improved PK and PD effects.

A representative example of dermal-access microdevice comprising a single needle were prepared from 34 gauge steel stock (MicroGroup, Inc., Medway, Mass.) and a single 28° bevel was ground using an 800 grit carborundum grinding wheel. Needles were cleaned by sequential sonication in acetone and distilled water, and flow-checked with distilled water. Microneedles were secured into small gauge catheter tubing (Maersk Medical) using UV-cured epoxy resin. Needle length was set using a mechanical indexing plate, with the hub of the catheter tubing acting as a depth-limiting control and was confirmed by optical microscopy. For experiments using needles of various lengths, the exposed needle lengths were adjusted to 0.5, 0.8, 1, 2 or 3 mm using the indexing plate. Connection to the fluid metering device, either pump or syringe, was via an integral Luer adapter at the catheter inlet. During injection, needles were inserted perpendicular to the skin surface, and were either held in place by gentle hand pressure for bolus delivery or held upright by medical adhesive tape for longer infusions. Devices were checked for function and fluid flow both immediately prior to and post injection. This Luer Lok single needle catheter design is hereafter designated SS1_34.

Yet another dermal-access array microdevices was prepared consisting of 1" diameter disks machined from acrylic polymer, with a low volume fluid path branching to each individual needle from a central inlet. Fluid input was via a low volume catheter line connected to a Hamilton microsyringe, and delivery rate was controlled via a syringe pump. Needles were arranged in the disk with a circular pattern of 15 mm diameter. Three-needle and six-needle arrays were constructed, with 12 and 7 mm needle-to-needle spacing, respectively. All array designs used single-bevel, 34 G stainless steel microneedles of 1 mm length. The 3-needle 12 mm spacing catheter-design is hereafter designated SS3_34B, 6-needle 7 mm spacing catheter-design is hereafter designated SS6_34A.

Yet another dermal-access array microdevices was prepared consisting of 11 mm diameter disks machined from acrylic polymer, with a low volume fluid path branching to each individual needle from a central inlet. Fluid input was via a low volume catheter line connected to a Hamilton microsyringe, and delivery rate was controlled via a syringe pump. Needles were arranged in the disk with a circular pattern of about 5 mm diameter. Three-needle arrays of about 4 mm spacing connected to a catheter as described above. These designs are hereafter designated SS3S_34_1, SS3S_34_2, and SS3S_34_3 for 1 mm, 2 mm, and 3 mm needle lengths respectively.

Yet another dermal-access ID infusion device was constructed using a stainless steel 30 gauge needle bent at near the tip at a 90-degree angle such that the available length for skin penetration was 1-2 mm. The needle outlet (the tip of the needle) was at a depth of 1.7-2.0 mm in the skin when the needle was inserted and the total exposed height of the needle outlet 1.0-1.2 mm. This design is hereafter designated SSB1_30.

Example I

Slow-infusion ID insulin delivery was demonstrated in swine using a hollow, silicon-based single-lumen microneedle (2 mm total length and 200×100 µm OD, corresponding to about 33 gauge) with an outlet 1.0 µm from the tip (100 µm exposed height), was fabricated using processes known in the art (U.S. Pat. No. 5,928,207) and mated to a microbore catheter (Disetronic). The distal end of the microneedle was placed into the plastic catheter and cemented in place with epoxy resin to form a depth-limiting hub. The needle outlet was positioned approximately 1 mm beyond the epoxy hub, thus limiting penetration of the needle outlet into the skin to approximately 1 mm., which corresponds to the depth of the intradermal space in swine. The catheter was attached to a MiniMed 507 insulin pump for control of fluid delivery. The distal end of the microneedle was placed into the plastic catheter and cemented in place with epoxy resin to form a depth-limiting hub. The needle outlet was positioned approximately 1 mm beyond the epoxy hub, thus limiting penetration of the needle outlet into the skin to approximately 1 mm., which corresponds to the depth of the intradermal space in swine. The patency of the fluid flow path was confirmed by visual observation, and no obstructions were observed at pressures generated by a standard 1-cc syringe. The catheter was connected to an external insulin infusion pump (MiniMed 507) via the integral Luer connection at the catheter outlet. The pump was filled with Humalog™ (Lispro) insulin (Eli Lilly, Indianapolis, Ind.) and the catheter and microneedle were primed with insulin according to the manufacturer's instructions. Sandostatin® (Sandoz, East Hanover, N.J.) solution was administered via IV infusion to anesthetized swine to suppress basal pancreatic function and insulin secretion. After a suitable induction period and baseline sampling, the primed microneedle was inserted perpendicular to the skin surface in the flank of the animal up to the hub stop. Insulin infusion at a rate of 2 U/hr was used and maintained for 4 hr. Blood samples were periodically withdrawn and analyzed for serum insulin concentration and blood glucose values. Baseline insulin levels before infusion were at the background detection level of the assay. After initiation of the infusion, serum insulin levels showed an increase that was commensurate with the programmed infusion rates. Blood glucose levels also showed a corresponding drop relative to negative controls (NC) without insulin infusion and this drop was improved relative to conventional SC infusion. In this experiment, the microneedle was demonstrated to adequately breach the skin barrier and deliver a drug in vivo at pharmaceutically relevant rates. The ID infusion of insulin was demonstrated to be a pharmacokinetically acceptable administration route, and the pharmacodynamic response of blood glucose reduction was also demonstrated. Calculated PK parameters for ID infusion indicate that insulin is absorbed much faster than via than SC administration. Absorption from the ID space begins almost immediately: the lag time prior to absorption ($t_{lag}$) was 0.88 vs. 13.6 min for ID and SC respectively. Also the rate of uptake from the administration site is increased by approximately 3-fold, $k_a$=0.0666 vs. 0.0225 min$^{-1}$ for ID and SC respectively. The bioavailability of insulin delivered by ID administration is increasedaproximately 1.3 fold greater than SC administration.

Example II

Figure 2:
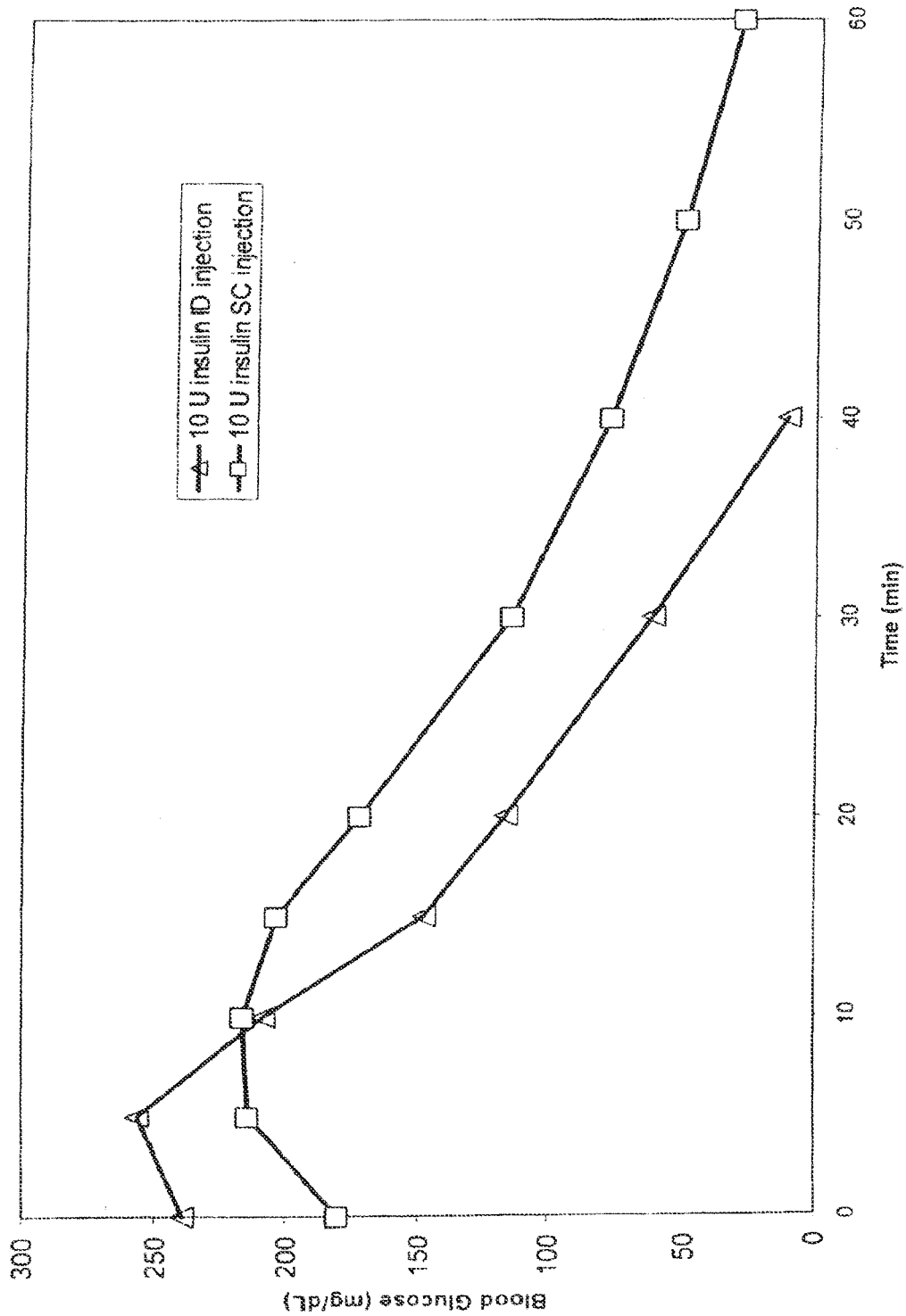
FIG. 2 shows a time course of blood glucose levels of intradermal versus subcutaneous bolus administration of fast-acting insulin.

Bolus delivery of Lilly Lispro fast acting insulin was performed using ID and SC bolus administration. The ID injection microdevice was dermal access array design SS3_34. 10 international insulin units (U) corresponding to 100 uL volume respectively, were administered to diabetic Yucatan Mini swine. Test animals had been previously been rendered diabetic by chemical ablation of pancreatic islet cells, and were no longer able to secrete insulin. Test animals received their insulin injection either via the microneedle array or via a standard 30 G×½ in. needle inserted laterally into the SC tissue space. Circulating serum insulin levels were detected using a commercial chemiluminescent assay kit (Immulite, Los Angeles, Calif.) and blood glucose values were determined using blood glucose strips. ID injections were accomplished via hand pressure using an analytical microsyringe and were administered over approximately 60 sec. By comparison, SC dosing required only 2-3 sec. Referring to FIG. 1, it is shown that serum insulin levels after bolus administration demonstrate more rapid uptake and distribution of the injected insulin when administered via the ID route. The time to maximum concentration ($T_{max}$) is shorter and the maximum concentration obtained ($C_{max}$) is higher for ID vs. SC administration. In addition, FIG. 2 also demonstrates the pharmacodynamic biological response to the administered insulin, as measured by the decrease in blood glucose (BG), showed faster and greater changes in BG since more insulin was available early after ID administration.

Example III

Figure 3:
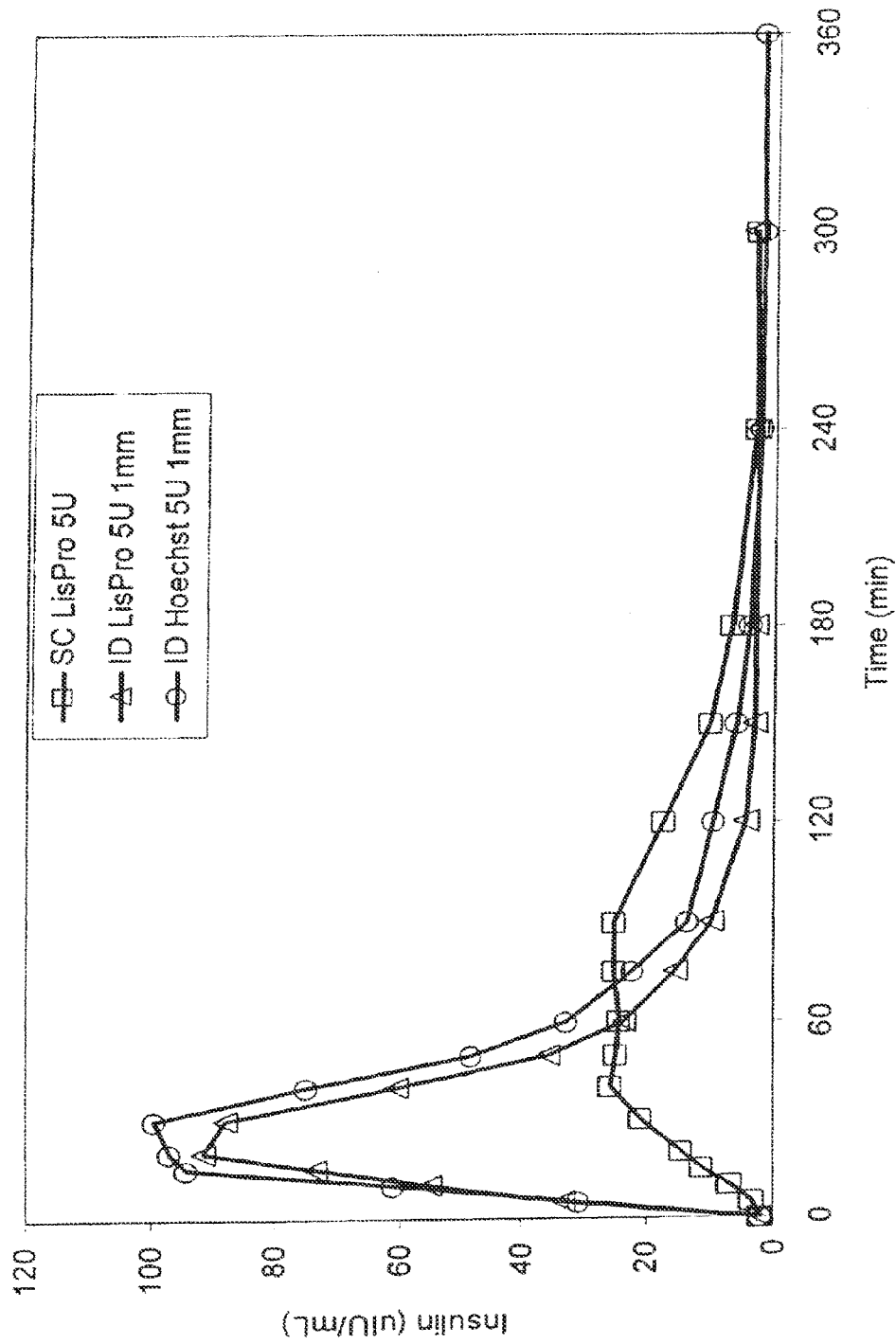
FIG. 3 shows a comparison of bolus ID dosing of fast-acting versus regular insulin.

Lilly Lispro is regarded as fact acting insulin, and has a slightly altered protein structure relative to native human insulin. Hoechst regular insulin, maintains the native human insulin protein structure that is chemically similar, but has slower uptake than Lispro when administered by the traditional SC route. Both insulin types were administered in bolus via the ID route to determine if any differences in uptake would be discernable by this route. 5 U of either insulin type were administered to the ID space using dermal access microdevice design SS3_34. The insulin concentration verses time data shown in FIG. 3. When administered by the ID route the PK profiles for regular and fast-acting insulin were essentially identical, and both insulin types exhibited faster uptake than Lispro given by the traditional SC route. This is evidence that the uptake mechanism for ID administration is less affected by minor biochemical changes in the administered substance, and that ID delivery provides an advantageous PK uptake profile for regular insulin that is superior to SC administered fast-acting insulin.

Example IV

Figure 4:
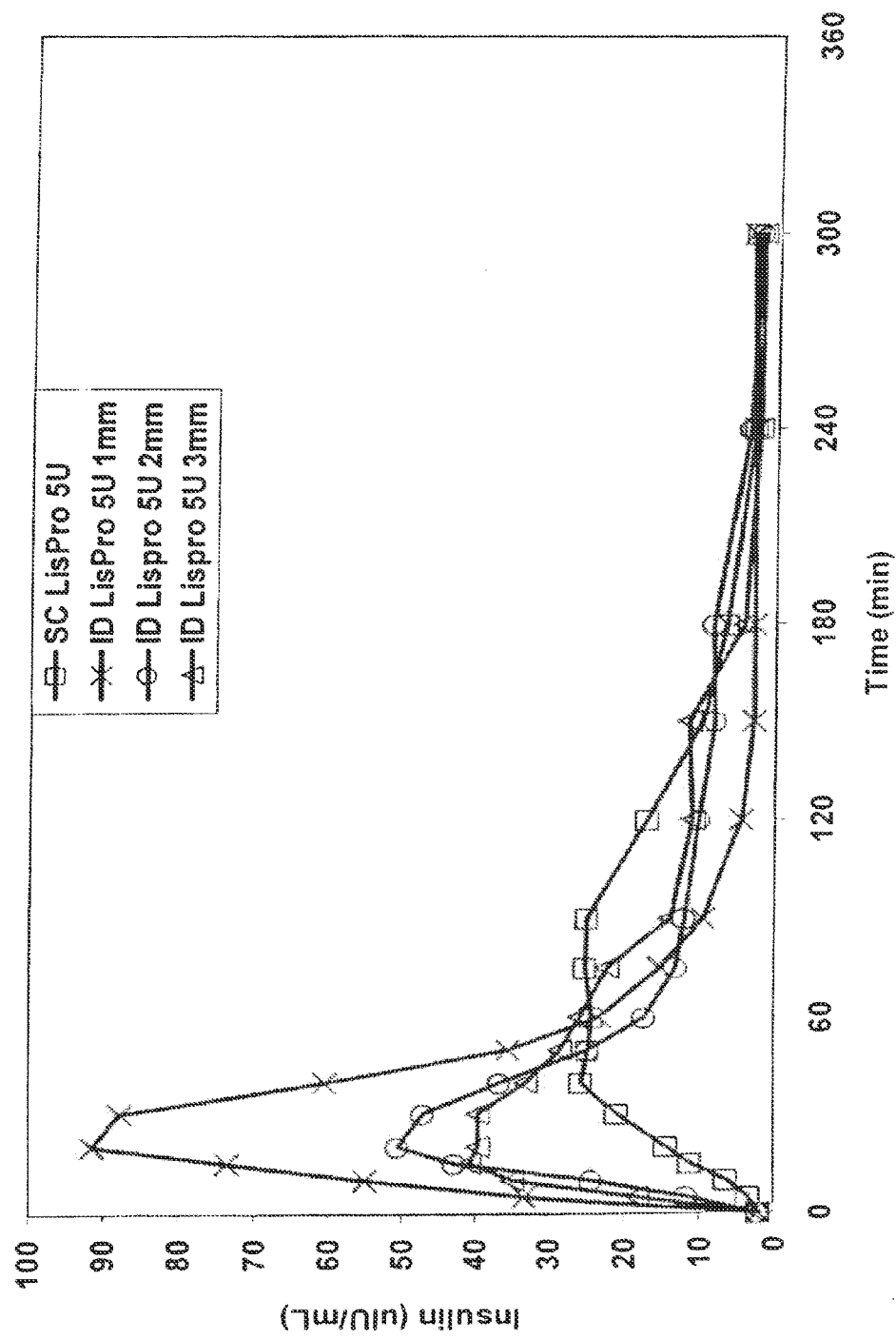
FIG. 4 shows the effects of different intradermal injection depths for bolus dosing of fast-acting insulin on the time course of insulin levels.

Bolus delivery of Lilly Lispro fast-acting insulin via microneedle arrays having needles of various lengths was conducted to demonstrate that the precise deposition of drug into the dermal space is necessary to obtain the PK advantages and distinctions relative to SC. Thus, 5 U of Lilly Lispro fast-acting insulin was administered using dermal access design SS3_34. Additional microdevices of the same needle array configuration were fabricated whereby exposed needle lengths of the microdevice array were lengthened to include arrays with needles lengths of 2 and 3 mm. The average total dermal thickness in Yucatan Mini swine ranges from 1.5-2.5 mm. Therefore insulin deposition is expected to be into the dermis, approximately at the dermal/SC interface, and below the dermis and within the SC for 1 mm, 2 mm, and 3 mm length needles respectively. Bolus insulin administration was as described in EXAMPLE II. Average insulin concentrations verses time are shown in FIG. 4. The data clearly shows as microneedle length is increased, the resulting PK profile begins to more closely resemble SC administration. This data demonstrates the benefits of directly targeting the dermal space, such benefits include rapid uptake and distribution, and high initial concentrations. Since the data are averages of multiple examples, they do not show the increased inter-individual variability in PK profiles from longer 2 and 3 mm microneedles. This data demonstrates that since skin thickness may vary both between individuals and even within a single individual, shorter needle lengths that accurately target the dermal space are more reproducible in their PK profile since they are depositing the drug more consistently in the same tissue compartment. This data demonstrates longer microneedles that deposit or administer substances deeper into the dermal space, or partially or wholly into the SC space, mitigate or eliminate the PK advantages in comparison to shallow, directly targeted administrations to the highly vascularized dermal region.

Example V

Figure 5:
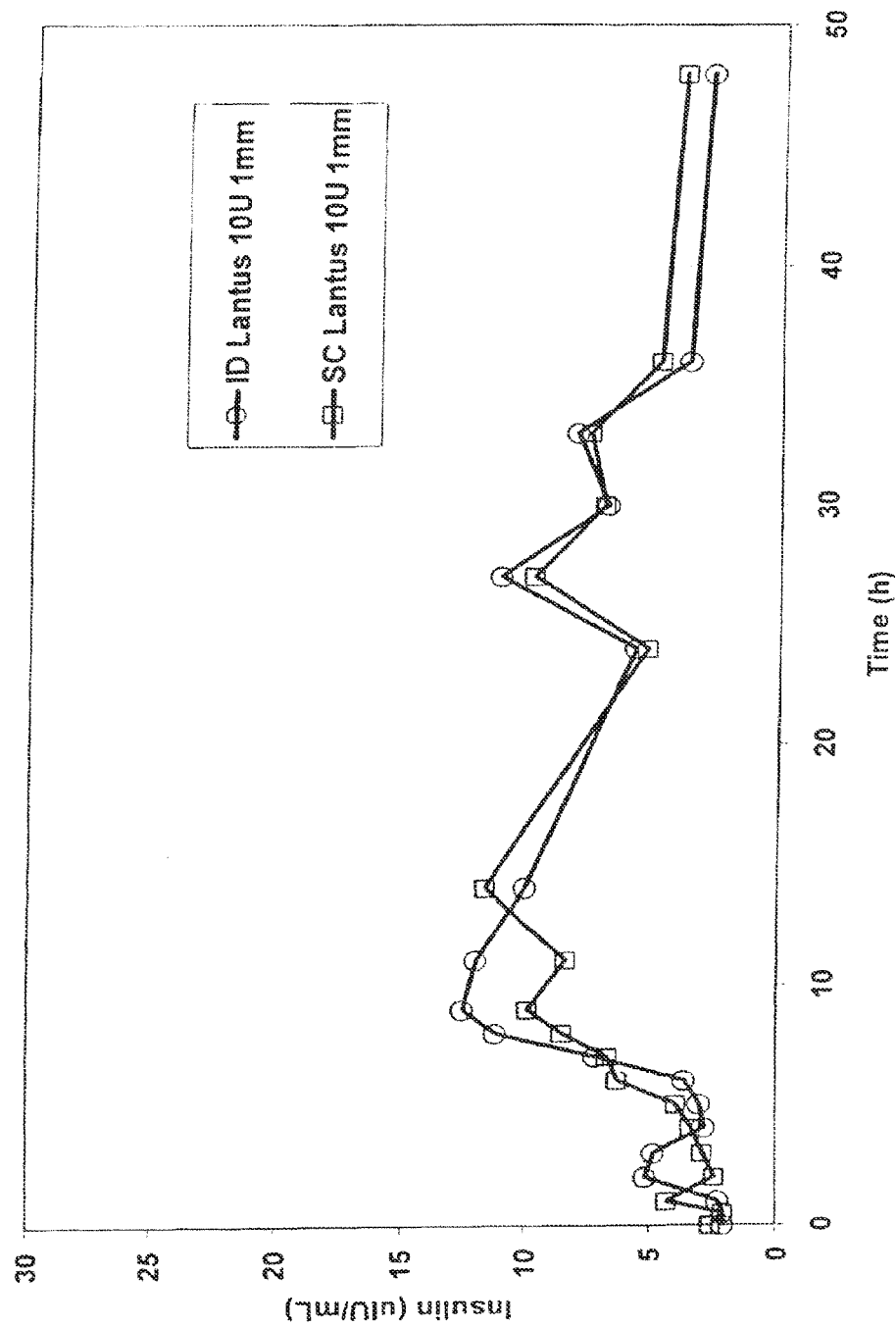
FIG. 5 shows a comparison of the time course of insulin levels for bolus dosing of long-acting insulin administered subcutaneously or intradermally.

Bolus delivery of Lantus long-acting insulin was delivered via the ID route. Lantus is an insulin solution that forms microprecipitates at the administration site upon injection. These microparticulates undergo slow dissolution within the body to provide (according to the manufacturer's literature) a more stable low level of circulating insulin than other current long-acting insulin such as crystalline zinc precipitates (e.g. Lente, NPH). Lantus insulin (10 U dose, 100 uL) was administered to diabetic Yucatan Mini pigs using the dermal access design SS3_34 and by the standard SC method as previously described. Referring to FIG. 5, when administered via the ID route, similar PK profiles were obtained relative to SC. Minor distinctions include a slightly higher "burst" immediately after the ID insulin delivery. This demonstrates that the uptake of even very high molecular weight compounds or small particles is achievable via ID administration. More importantly this supports the fact that the biological clearance mechanism in the body is not appreciably changed by the administration route, nor is the way in which that the drug substance is utilized. This is extremely important for drugs compounds that have a long circulating half-life (examples would be large soluble receptor compounds or other antibodies for cancer treatment, or chemically modified species such as PEGylated drugs).

Example VI

Figure 6:
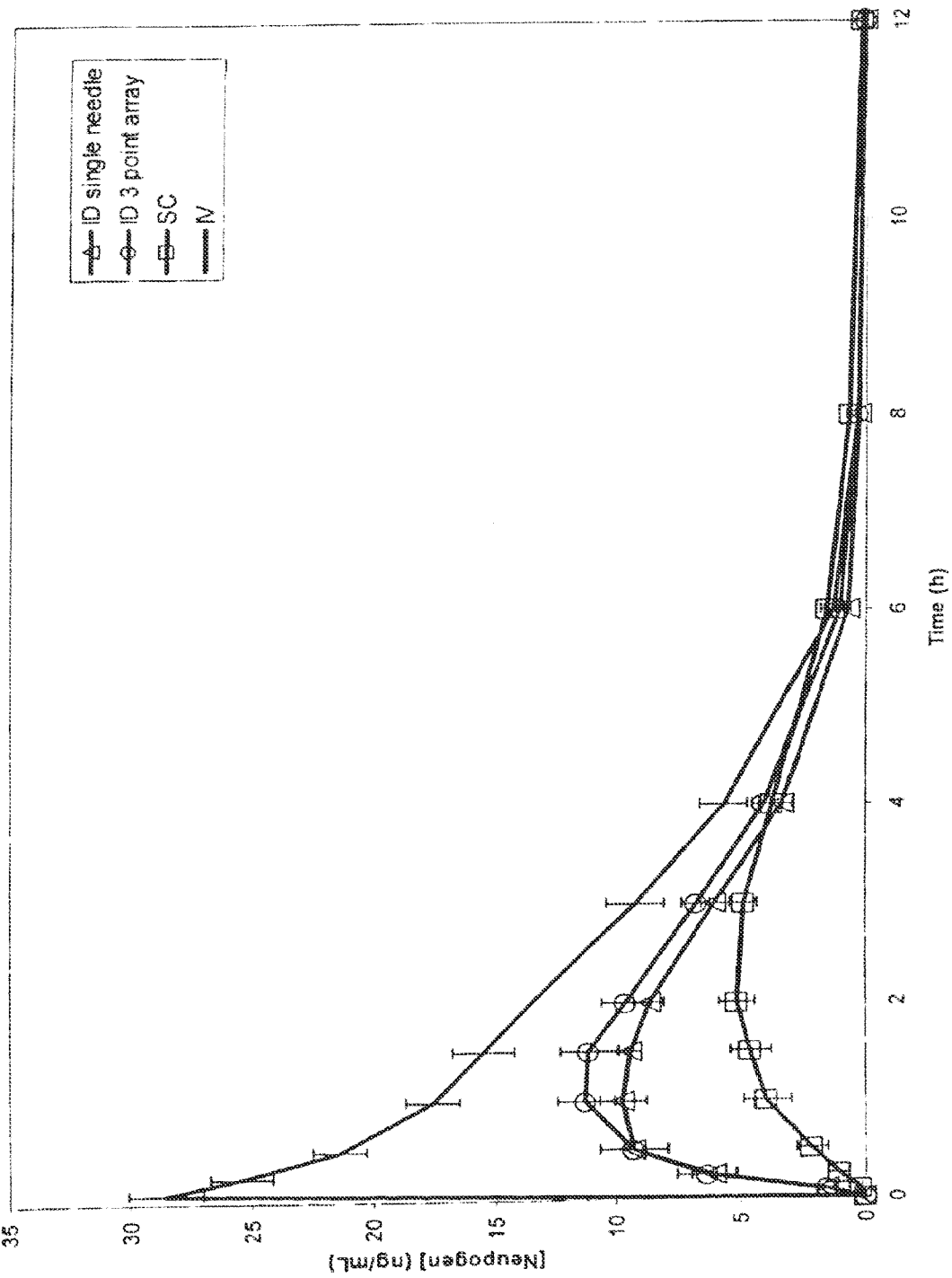
FIGS. 6 and 7 show a comparison of the pharmacokinetic availability and the pharmacodynamic results of granulocyte colony stimulating factor delivered intradermally with a single needle or three point needle array, subcutaneously, or intravenously.
Figure 7:
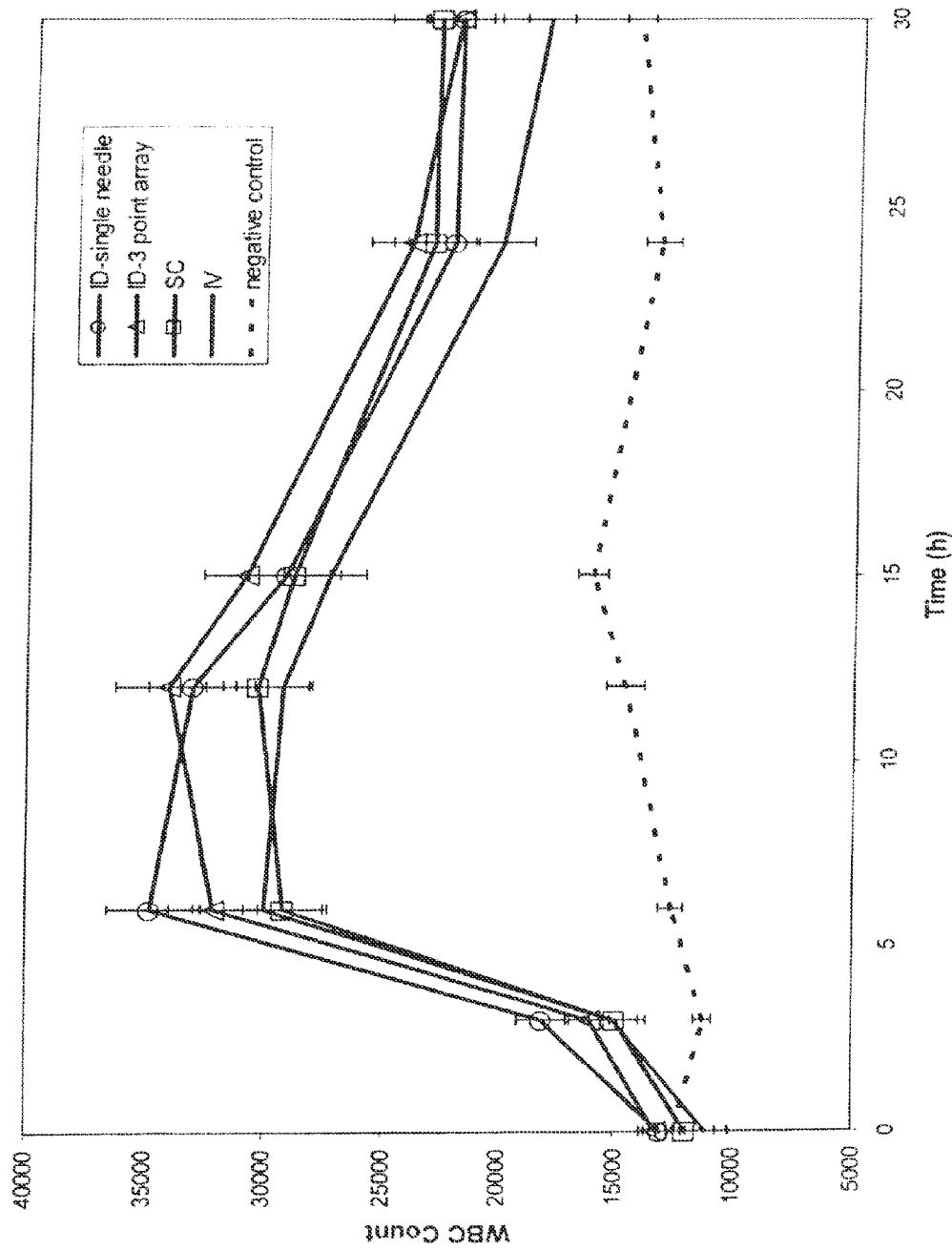
Figure 8:
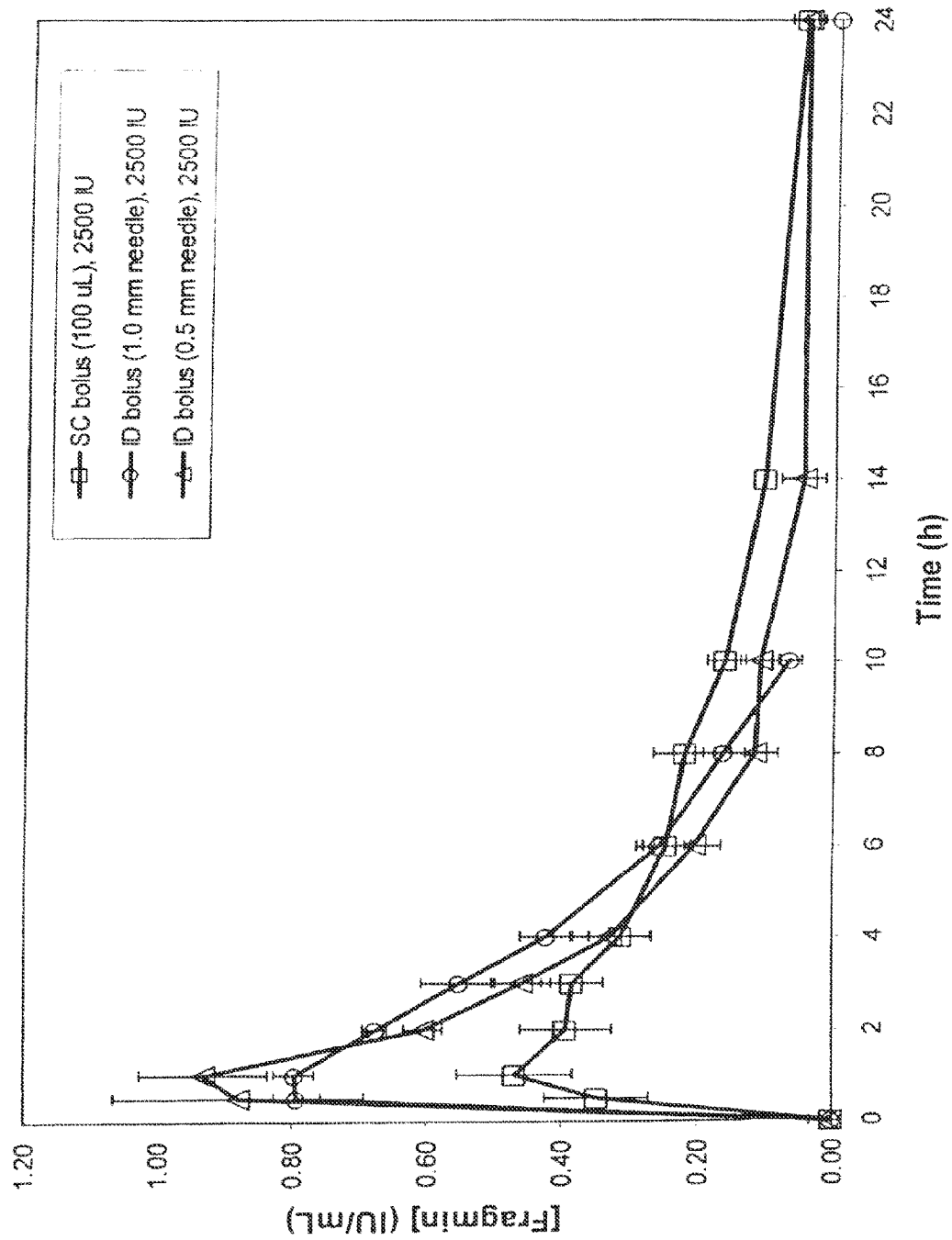
FIGS. 8, 9 and 10 show a comparison of low molecular weight heparin intradermal delivery by bolus, short duration, long duration infusion with comparison to subcutaneous infusion.
Figure 9:
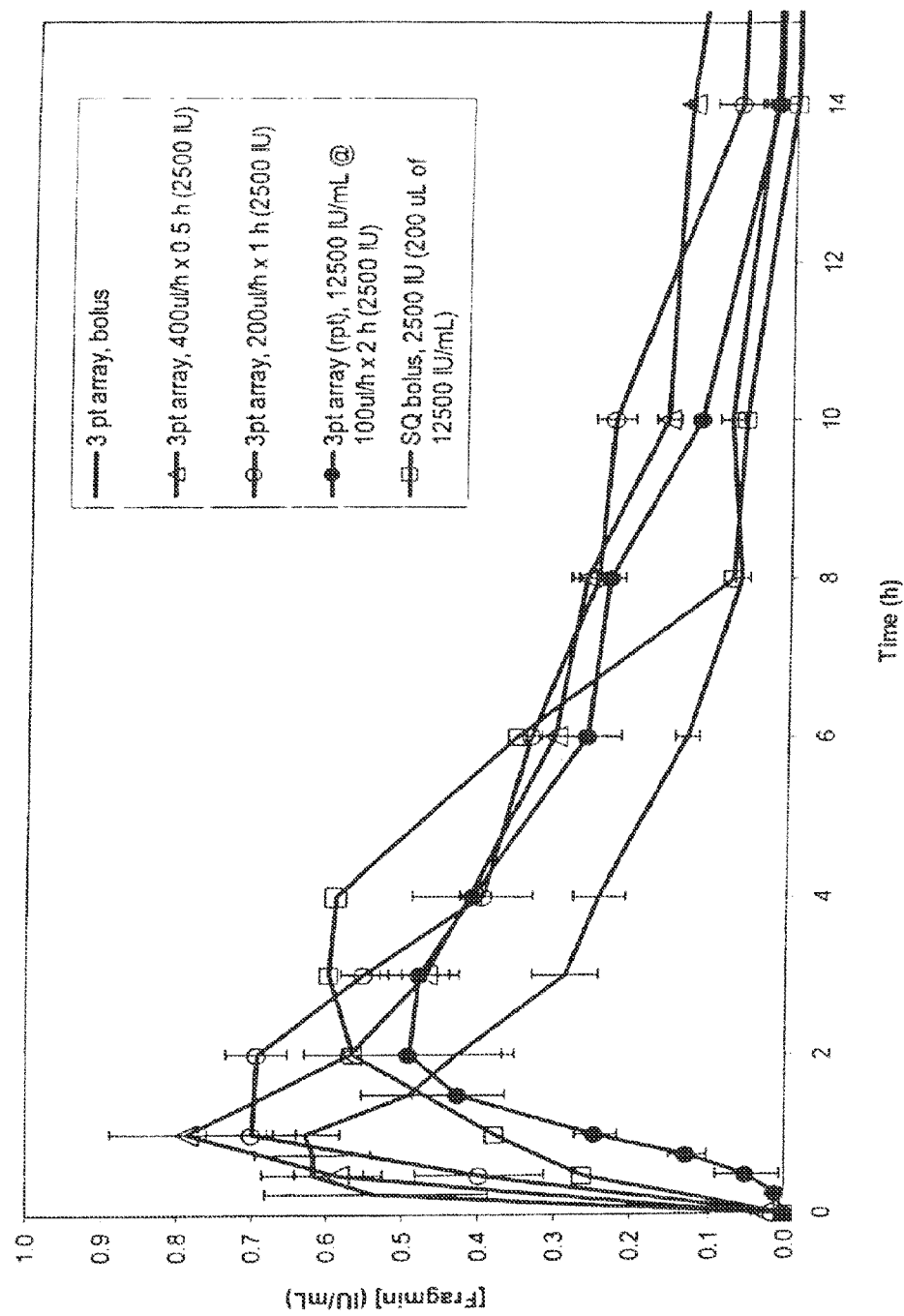
Figure 10:
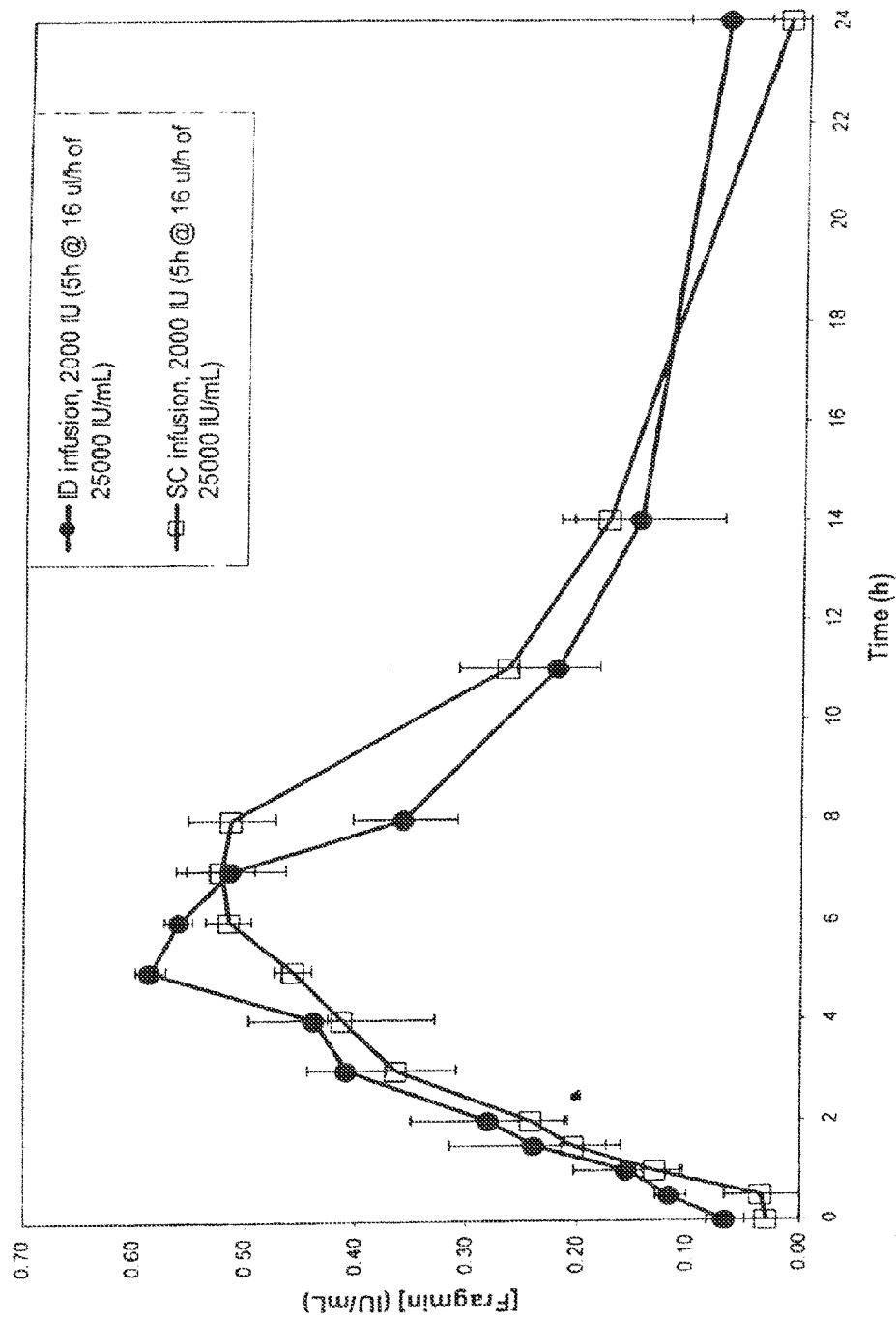

Bolus ID delivery of human granulocyte colony stimulating factor (GCSF) (Neupogen) was administered via dermal access microdevice designs SS3_34B (array) or SS1_34 (single needle) to Yucatan minipigs. Delivery rate was controlled via a Harvard syringe pump and was administered over a 1-2.5 min period. FIG. 6 shows the PK availability of GCSF in blood plasma as detected by an ELISA immunoassay specific for GCSF. Administration via IV and SC delivery was performed as controls. Referring to FIG. 6 bolus ID delivery of GCSF shows the more rapid uptake associated with ID delivery. $C_{max}$ is achieved at approximately 30-90 minutes vs. 120 min for SC. Also the bioavailability is dramatically increased by an approximate factor of 2 as evidenced by the much higher area under the curve (AUC). Circulating levels of GCSF are detectable for an extended period, indicting that ID delivery does not alter the intrinsic biological clearance mechanism or rate for the drug. These data also show that device design has minimal effect on the rapid uptake of drug from the ID space. The data referred to in FIG. 7 also shows the degree and time course of white blood cell expansion as a result of GCSF administration with respect to a negative control (no GCSF administered). White blood cell (WBC) counts were determined by standard cytometric clinical veterinary methods ID delivery exhibits the same clinically significant biological outcomes. Although all delivery means give approximately equal PD outcomes, this data suggests ID delivery could enable use half the dose to achieve essentially the same physiological result in comparison to SC, due to approximately 2-fold bioavailability increase.

Example VII

An ID administration experiment was conducted using a peptide drug entity: human parathyroid hormone 1-34 (PTH). PTH was infused for a 4 h period, followed by a 2 h clearance. Control SC infusion was through a standard 31-gauge needle inserted into the SC space lateral to the skin using a "pinch-up" technique. ID infusion was through dermal access microdevice design SSB1_30 (a stainless steel 30-gauge needle bent at the tip at a 90° angle such that the available length for skin penetration was 1-2 mm). The needle outlet (the tip of the needle) was at a depth of 1.7-2.0 mm in the skin when the needle was inserted. A 0.64 mg/mL PTH solution was infused at a rate of 75 µL/hr. Flow rate was controlled via a Harvard syringe pump. Weight normalized PTH plasma levels are shown in Figure XX. {The weight normalized delivery profiles show a larger area under the curve (AUC) indicating higher bioavailability, higher peak values at earlier sampling timepoints (e.g. 15 and 30 min) indicating more rapid onset from ID delivery, and rapid decrease following termination of infusion (also indicative of rapid uptake without a depot effect).}

The above examples and results demonstrate the inventive delivery method using multi-point array ID administration and single needle ID administration results in more rapid uptake with higher $C_{max}$ than SC injection. ID uptake and distribution is ostensibly unaffected by device geometry parameters, using needle lengths of about 0.5 to about 1.7 mm, needle number and needle spacing. No concentration limit for biological absorption was found and PK profiles were dictated principally by the concentration-based delivery rate. The primary limitations of ID administration are the total volume and volumetric infusion-rate limits for leak-free instillation of exogenous substances into a dense tissue compartment. Since absorption of drugs from the ID space appears to be insensitive to both device design and volumetric infusion rate, numerous formulation/device combinations can be used to overcome this limitations and provide the required or desired therapeutic profiles. For example, volume limited dosing regimens can be circumvented either by using more concentrated formulations or increasing the total number of instillation sites. In addition, effective PK control is obtained by manipulating infusion or administration rate of substances.

In general, ID delivery as taught by the methods described hereto via dermal access microneedle devices provides a readily accessible and reproducible parenteral delivery route, with high bioavailability, as well as the ability to modulate plasma profiles by adjusting the device infusion parameters, since uptake is not rate-limited by biological uptake parameters.

In the previously described examples, the methods practiced by the invention demonstrate the ability to deliver a drug in vivo with greatly improved pharmaceutically relevant rates. This data indicates an improved pharmacological result for ID administration as taught by the methods described of other drugs in humans would be expected according to the methods of the invention.

All references cited in this specification are hereby incorporated by reference. The discussion of the references herein is intended merely to summarize the assertions made by their authors and no admission is made that any reference constitutes prior art relevant to patentability. Applicants reserve the right to challenge the accuracy and pertinency of the cited references.

What is claimed is:

1. A method for administration of a drug to a human subject, comprising delivering the drug through the lumen of a hollow needle into an intradermal compartment of the human subject's skin, which method comprises
   (a) inserting the needle into the subject's skin so that the needle penetrates the intradermal compartment, and the needle's outlet depth and exposed height of the outlet are located within the intradermal compartment, wherein the outlet has an exposed height of 0 to about 1 mm; and
   (b) delivering the drug through the lumen of the needle with the application of pressure in an amount effective to control the rate of delivery of the drug,
   so that the drug is delivered through the lumen of the needle into the intradermal compartment and distributed systemically exhibiting any one of the following improved pharmacokinetic parameters as compared to subcutaneous delivery:
   (i) a higher maximum plasma concentration and a higher bioavailability;
   (ii) a higher maximum plasma concentration and a decreased time to elicit a minimally detectable blood or plasma concentration;
   (iii) a higher bioavailability and a decreased time to elicit a minimally detectable blood or plasma concentration;
   (iv) a higher bioavailability and decreased time to maximal plasma concentration; or
   (v) a decreased time to elicit a minimally detectable blood or plasma concentration and decreased time to maximal plasma concentration;
   wherein the drug is a small molecule, a macromolecule, or a monoclonal antibody.

2. The method of claim 1, wherein the needle is selected from the group consisting of microneedles, catheter needles, and injection needles.

3. The method of claim 1, wherein a single needle is inserted.

4. The method of claim 1, wherein multiple needles are inserted.

5. The method of claim 1, wherein the drug is administered as a solution delivered by pressure directly on the solution.

6. The method of claim 1, wherein the needle has a length from about 0.5 to about 1.7 mm.

7. The method of claim 1, wherein the needle's outlet depth is between about 0.3 mm to 2 mm when the needle is inserted.

8. The method of claim 1, wherein the outlet has an exposed height of 0 mm.

9. The method of claim 1, wherein the delivery rate is controlled by spacing of multiple needles.

10. The method of claim 1, wherein the improved pharmacokinetic parameters are a higher maximum plasma concentration and a higher bioavailability.

11. The method of claim 1, wherein the improved pharmacokinetic parameters are a higher maximum plasma concentration and a decreased time to elicit a minimally detectable blood or plasma concentration.

12. The method of claim 1, wherein the improved pharmacokinetic parameters are a higher bioavailability and a decreased time to elicit a minimally detectable blood or plasma concentration.

13. The method of claim 1, wherein the improved pharmacokinetic parameters are a higher bioavailability and decreased time to maximal plasma concentration.

14. The method of claim 1, wherein the improved pharmacokinetic parameters are a decreased time to elicit a minimally detectable blood or plasma concentration and decreased time to maximal plasma concentration.

15. The method of claim 1, wherein the drug is a small molecule.

16. The method of claim 15, wherein the small molecule is butorphanol, a COX-II inhibitor, a dermatological agent, dihydroergotamine, a dopamine agonist, a dopamine antagonist, granisetron, metoclopramide, midazolam, an agent for the common cold, an anti-addiction agent, an anti-allergy agent, an anti-emetic, an anti-obesity agent, an anti-osteoporotic agent, an anti-infective, an analgesic, an anesthetic, an anorexic agent, an anti-arthritic agent, an anti-asthmatic agent, an anti-convulsant, an anti-depressant, an anti-diabetic agent, an anti-histamine, an anti-inflammatory agent, an antimigraine preparation, an anti-motion sickness preparation, an anti-nauseant, an anti-neoplastic agent, an anti-parkinsonism drug, an anti-pruritic, an anti-psychotic, an anti-pyretic, an anti-cholinergic, a benzodiazepine antagonist, a vasodilator, a bone stimulating agent, a central nervous system stimulant, a hormone, a hypnotic, an immunosuppressive, a muscle relaxant, a parasympatholytic, a parasympathomimetric, a prostaglandin, a psychostimulant, a sedative, or a tranquilizer.

17. The method of claim 1, wherein the drug is a macromolecule.

18. The method of claim 17, wherein the macromolecule is inulin, adrenocorticotropic hormone (ACTH), luteinizing hormone-releasing hormone, growth hormone-releasing hormone, cholecystokinin, parathyroid hormone or fragments thereof, thyroid releasing hormone or analogs thereof, secretin, alpha-1 anti-trypsin, an anti-angiogenesis agent, calcitonin or analogs thereof, ceredase, enkephalins or other opioid peptides, epidermal growth factors, erythropoietin or analogs thereof, follicle stimulating hormone, granulocyte colony-stimulating factor (G-CSF), glucagon, granulocyte-macrophage colony-stimulating factor (GM-CSF), growth hormone or analogs thereof, a growth hormone antagonist, hirudin or analogs thereof, IgE suppressor, insulin, insulinotropin or analogs thereof, insulin-like growth factor, interferon, interleukin, luteinizing hormone, luteinizing hormone releasing hormone or analogs thereof, heparins, low molecular weight heparin, or macrophage colony-stimulating factor (M-CSF).

19. The method of claim 1, wherein the drug is a monoclonal antibody.

20. The method of claim 19, wherein the monoclonal antibody is a peglyated antibody, a pegylated protein or a protein modified with hydrophilic or hydrophobic polymers or additional functional groups, a fusion protein, or a single chain antibody fragment.

* * * * *

UNITED STATES PATENT AND TRADEMARK OFFICE
CERTIFICATE OF CORRECTION

PATENT NO. : 9,242,052 B2
APPLICATION NO. : 14/215271
DATED : January 26, 2016
INVENTOR(S) : Ronald J. Pettis et al.

It is certified that error appears in the above-identified patent and that said Letters Patent is hereby corrected as shown below:

Column 21, Line 32, Claim 16, delete "antimigraine" and insert -- anti-migraine --

Column 22, Lines 4-5, Claim 16, delete "parasympathomimetric," and insert -- parasympathomimetic, --

Column 22, Line 29, Claim 20, delete "peglyated" and insert -- pegylated --

Signed and Sealed this
Seventh Day of June, 2016

Michelle K. Lee
*Director of the United States Patent and Trademark Office*